(12) United States Patent
Liu et al.

(10) Patent No.: US 12,394,535 B2
(45) Date of Patent: Aug. 19, 2025

(54) RADIATION TREATMENT SYSTEM AND OPERATING METHOD THEREOF

(71) Applicant: SHANGHAI UNITED IMAGING HEALTHCARE CO., LTD., Shanghai (CN)

(72) Inventors: Yanfang Liu, Shanghai (CN); Li Wang, Shanghai (CN); Cheng Ni, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 460 days.

(21) Appl. No.: 17/649,062

(22) Filed: Jan. 26, 2022

(65) Prior Publication Data

US 2022/0143426 A1     May 12, 2022

Related U.S. Application Data

(63) Continuation of application No. PCT/CN2019/097998, filed on Jul. 26, 2019.

(51) Int. Cl.
*A61N 5/06*     (2006.01)
*A61N 5/01*     (2006.01)
(Continued)

(52) U.S. Cl.
CPC ............ *G21K 1/02* (2013.01); *A61N 5/1045* (2013.01)

(58) Field of Classification Search
CPC .......... A61N 5/1045; A61N 5/06; A61N 5/01; A61N 5/10; A61N 7/00; A61N 1/00;
(Continued)

(56) References Cited

U.S. PATENT DOCUMENTS 5,144,647 A     9/1992    Kikuchi
5,591,983 A     1/1997    Yao
(Continued)

FOREIGN PATENT DOCUMENTS

AU     2017208382 A1     8/2017
CN     109224318 A     1/2019
EP     2687259 A1     1/2014

OTHER PUBLICATIONS

International Search Report in PCT/CN2019/097998 mailed on Apr. 26, 2020, 5 pages.
(Continued)

*Primary Examiner* — Daquan Zhao
(74) *Attorney, Agent, or Firm* — METIS IP LLC

(57) ABSTRACT

The present disclosure relates to a radiation treatment system. The radiation treatment system may include an MLC having at least one layer of leaves and at least one block. Each of the at least one layer of leaves may include a first group of leaves and a second group of leaves. At least a portion of the leaves may be movable to block pathways of a first portion of the radiation beams within a radiation area. A second portion of the radiation beams may be incident at a treatment region of the radiation treatment system. The MLC may be situated in a first plane. The at least one block may be situated in a second plane different from the first plane. The at least one block may be configured to shield at least a portion of leaking radiation beams within an end area.

20 Claims, 12 Drawing Sheets

(51) Int. Cl.
*A61N 5/10* (2006.01)
*G21K 1/02* (2006.01)
*A61N 7/00* (2006.01)

(58) Field of Classification Search
CPC ...... A61N 2/00; A61N 5/00; A61N 2005/002;
G21K 1/02; G21K 1/046; G21K 1/00;
G21K 4/00; G21K 5/00; G21K 7/00;
G21K 2201/00; G21K 2207/00
USPC .......................................... 348/61, 68, 76, 77
See application file for complete search history.

(56) References Cited

U.S. PATENT DOCUMENTS

| | | | |
|---|---|---|---|
| 6,266,393 | B1 | 7/2001 | Ein-Gal |
| 6,459,769 | B1 | 10/2002 | Cosman |
| 6,600,810 | B1 | 7/2003 | Hughes |
| 8,067,751 | B2 | 11/2011 | Mohr |
| 9,443,633 | B2 | 9/2016 | Orton et al. |
| 10,518,110 | B1* | 12/2019 | Jimenez-Carvajal ........................ A61N 5/1075 |
| 2001/0043669 | A1 | 11/2001 | Ein-Gal |
| 2008/0073591 | A1 | 3/2008 | Mohr |
| 2008/0165930 | A1 | 7/2008 | Perkins |
| 2012/0012763 | A1 | 1/2012 | Kuusela et al. |
| 2012/0043482 | A1* | 2/2012 | Prince ................... G21K 1/046 250/505.1 |
| 2012/0105969 | A1 | 5/2012 | Ehringfeld et al. |
| 2012/0256103 | A1 | 10/2012 | Luzzara |
| 2014/0112453 | A1 | 4/2014 | Prince et al. |
| 2015/0273239 | A1 | 10/2015 | Hsu et al. |
| 2017/0084359 | A1 | 3/2017 | Constantin et al. |
| 2017/0087386 | A1* | 3/2017 | Mellenberg .......... A61N 5/1045 |
| 2017/0143995 | A1 | 5/2017 | Bergfjord |
| 2017/0148536 | A1 | 5/2017 | Kawrykow et al. |
| 2018/0078784 | A1 | 3/2018 | Schnarr |
| 2018/0161602 | A1 | 6/2018 | Kawrykow et al. |
| 2018/0261351 | A1 | 9/2018 | Kawrykow et al. |
| 2019/0001153 | A1* | 1/2019 | Jones ..................... G21K 1/046 |
| 2019/0046815 | A1 | 2/2019 | Ollila et al. |
| 2019/0175944 | A1* | 6/2019 | Towe .................. A61N 5/1045 |
| 2019/0209864 | A1 | 7/2019 | Stahl et al. |
| 2019/0240209 | A1 | 8/2019 | Kwon et al. |
| 2019/0240509 | A1* | 8/2019 | Kuusela ............... A61N 5/1045 |
| 2020/0185119 | A1* | 6/2020 | Stahl ..................... G21K 1/046 |

OTHER PUBLICATIONS

Written Opinion in PCT/CN2019/097998 mailed on Apr. 26, 2020, 4 pages.
International Search Report in PCT/CN2020/097346 mailed on Sep. 25, 2020, 5 pages.
Written Opinion in PCT/CN2020/097346 mailed on Sep. 25, 2020, 5 pages.

* cited by examiner

RADIATION TREATMENT SYSTEM AND OPERATING METHOD THEREOF

CROSS-REFERENCE TO RELATED APPLICATIONS

This application is a Continuation of International Application No. PCT/CN2019/097998, filed on Jul. 26, 2019, the contents of which are hereby incorporated by reference.

TECHNICAL FIELD

The present disclosure generally relates to radiotherapy, and more specifically relates to a radiation treatment system, and a method for operating the radiation treatment system.

BACKGROUND

Radiotherapy is generally part of cancer treatment to control or kill, e.g., a tumor of an object, using ionizing radiation. A multi-leaf collimator (MLC) may be used to shape radiation to fit the shape of the tumor so that the tumor receives sufficient radiation. For instance, by moving at least one leaf of the MLC to at least one desired position, a treatment region conforming to the shape of the tumor may be formed. However, the MLC is likely to fail to block pathways of leaking radiation within a region other than the region of the tumor while moving the at least one leaf, which may cause damage to the normal tissues of the object. In some cases, a combination of the MLC and one or two pairs of collimation jaws may be provided. The one or two pairs of collimation jaws may be used cooperatively with the MLC to shape the radiation. Besides, the one or two pairs of collimation jaws may reduce at least a portion of the leaking radiation. However, the size and weight of the one or two pairs of collimation jaws may be relatively large, causing additional burden on a radiation treatment system for the radiotherapy. Thus, it is desirable to provide a radiation treatment system and/or methods for operating the radiation treatment system to more effectively block the pathways of leaking radiation other than in the treatment region.

SUMMARY

In a first aspect of the present disclosure, a radiation treatment system may be provided. The radiation treatment system may include a radiation source, a multi-leaf collimator (MLC), and at least one block. The radiation source may be configured to emit radiation beams. The MLC may be situated in a first plane. The MLC may include at least one layer of leaves. Each of the at least one layer of leaves may include a first group of leaves and a second group of leaves. At least a portion of the leaves may be movable to block pathways of a first portion of the radiation beams within a radiation area. A second portion of the radiation beams may be incident at a treatment region of the radiation treatment system. The at least one block may be situated in a second plane different from the first plane. The at least one block may be configured to shield at least a portion of leaking radiation beams within an end area.

In some embodiments, the MLC and the at least one block may be arranged along a direction of the radiation beams towards an object.

In some embodiments, the end area may include a first section that forms when one or more leaves of the first group of at least one of the at least one layer of leaves pass across a first line such that the first section is exposed to allow at least a portion of the first portion of the radiation beams to leak through.

In some embodiments, the first line may be a centerline of the radiation area. A length of at least one of the first group of leaves may be equal to a half of a length of the radiation area.

In some embodiments, the at least one block may include a first block and a second block situated in the second plane.

In some embodiments, at least one of the at least one block, or a portion thereof, may be movable.

In some embodiments, at least one of the at least one block may be fixed, and projection of the at least one of the at least one block on the first plane may at least partially overlap the MLC.

In some embodiments, a size of each of the at least one block may relate to at least one of: a first reference distance that at least one leaf of the first group of leaves is allowed to move, a second reference distance that at least one leaf of the second group of leaves is allowed to move, a size of each of the at least one layer of leaves, a length of at least one leaf of the first group of leaves, or a length of at least one leaf of the second group of leaves.

In a second aspect of the present disclosure, a method for operating a multi-leaf collimator (MLC) may be provided. The method may be implemented on a computing device having at least one processor, and at least one computer-readable storage medium. The MLC may include at least a first layer of leaves and a second layer of leaves. Each of the first layer of leaves and the second layer of leaves may include a first group of leaves and a second group of leaves. At least a portion of the leaves may be movable to block pathways of a first portion of the radiation beams within a radiation area. A second portion of the radiation beams may be incident at a treatment region of the radiation treatment system. The method may include determining whether a first region exists. The first region may form when one or more leaves of the first group of the first layer of leaves pass across a first line such that the first region is exposed to allow at least a portion of the first portion of the radiation beams to leak through. The method may also include causing, based on a determination result, the second layer of leaves of the MLC to operate.

In some embodiments, the first line may be a centerline of the radiation area. A length of at least one of the first group of leaves may be equal to a half of a length of the radiation area.

In some embodiments, the determination result may include that the first region exists, and the causing the second layer of leaves of the MLC to operate may include causing one or more leaves of the second layer of leaves to move to shield at least a portion of radiation beams leaked through the first region.

In some embodiments, the determination result may include that the first region does not exist, and the causing the second layer of leaves of the MLC to operate may include causing one or more leaves of the second layer of leaves to move to block a part of the second portion of the radiation beams.

In a third aspect of the present disclosure, a method for operating a radiation treatment system. The method may be implemented on a computing device having at least one processor, and at least one computer-readable storage medium. The radiation treatment system may include a multi-leaf collimator (MLC) and at least one block. The MLC may include at least one layer of leaves. Each of the at least one layer of leaves may include a first group of leaves and a second group of leaves. At least a portion of the leaves may be movable to block pathways of a first portion of the radiation beams within a radiation area. A second portion of the radiation beams may be incident at a treatment region of the radiation treatment system. The method may include determining whether a first region exists. The first region may form when one or more leaves of the first group of the first layer of leaves pass across a first line such that the first region is exposed to allow at least a portion of the first portion of the radiation beams to leak through. The method may also include causing, based on a determination result, at least one of the at least one block or the second layer of leaves of the MLC to operate.

In some embodiments, the at least one block may be fixed in the second plane. Projection of the at least one of the at least one block may at least partially overlap the MLC.

In some embodiments, the determination result may include that the first region exists, and the causing at least one of the at least one block or the second layer of leaves of the MLC to operate may include causing one or more leaves of the second layer of leaves to move to block a part of the second portion of the radiation beams.

In some embodiments, the at least one block may be moveable, the determination result may include that the first region exists, and the causing at least one of the at least one block or the second layer of leaves of the MLC to operate may include determining whether the at least one block is able to move; and causing, based on a second determination result, the second layer of leaves to operate.

In some embodiments, the causing, based on a second determination result, the second layer of leaves to operate may include: in response to the second determination that the at least one block is able to move, causing the at least one block to shield at least a portion of the radiation beams that leak through the first region, and causing one or more leaves of the second layer of leaves to move to block a part of the second portion of the radiation beams; or in response to the second determination that the at least one block is unable to move, causing one or more leaves of the second layer of leaves to shield at least a portion of the radiation beams that leak through the first region.

In some embodiments, the determination result may include that the first region does not exist, and the causing at least one of the at least one block or the second layer of leaves of the MLC to operate may include: causing one or more leaves of the second layer of leaves to move to block a part of the second portion of the radiation beams.

In a fourth aspect of the present disclosure, a non-transitory computer readable medium may be provided. The non-transitory computer readable medium may include instructions being executed by at least one processor, causing the at least one processor to implement a method. A multi-leaf collimator (MLC) may include at least a first layer of leaves and a second layer of leaves. Each of the first layer of leaves and the second layer of leaves may include a first group of leaves and a second group of leaves. At least a portion of the leaves may be movable to block pathways of a first portion of the radiation beams within a radiation area. A second portion of the radiation beams may be incident at a treatment region of the radiation treatment system. The method may include determining whether a first region exists. The first region may form when one or more leaves of the first group of the first layer of leaves pass across a first line such that the first region is exposed to allow at least a portion of the first portion of the radiation beams to leak through. The method may also include causing, based on a determination result, the second layer of leaves of the MLC to operate.

In a fifth aspect of the present disclosure, a non-transitory computer readable medium may be provided. The non-transitory computer readable medium may include instructions being executed by at least one processor, causing the at least one processor to implement a method. A radiation treatment system may include a multi-leaf collimator (MLC) and at least one block. The MLC may include at least one layer of leaves. Each of the at least one layer of leaves may include a first group of leaves and a second group of leaves. At least a portion of the leaves may be movable to block pathways of a first portion of the radiation beams within a radiation area. A second portion of the radiation beams may be incident at a treatment region of the radiation treatment system. The method may include determining whether a first region exists. The first region may form when one or more leaves of the first group of the first layer of leaves pass across a first line such that the first region is exposed to allow at least a portion of the first portion of the radiation beams to leak through. The method may also include causing, based on a determination result, at least one of the at least one block or the second layer of leaves of the MLC to operate.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. The term "direction" may include the opposite direction of the direction and a plurality of directions that are parallel to the direction. The term "plane" may include both planar and curved or cylindrical planes. The direction may include both linear and arc trajectories. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
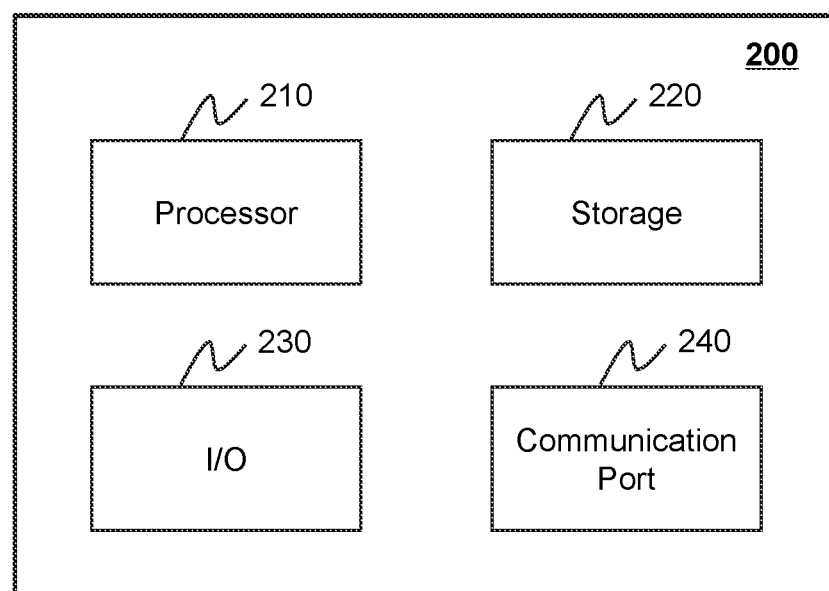
FIG. 2 is a schematic diagram illustrating exemplary hardware and/or software components of a computing device according to some embodiments of the present disclosure.

Generally, the word "module," "unit," or "block," as used herein, unless otherwise defined, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

A first aspect of the present disclosure relates to a radiation treatment system. A portion of the radiation treatment system may be configured to form an aperture through which a portion of radiation beams is delivered to a treatment region. In some embodiments, a lesion (e.g., the tumor) of the object may be located at the treatment region for radiotherapy. The treatment region and the aperture may conform to the shape of the lesion. The portion of the radiation treatment system may include an MLC and at least one block. The MLC may include at least one layer of leaves. Each of the at least one layer of leaves may include a plurality of leaves. In some cases, the MLC may fail to block pathways of leaking radiation beams within an end area in a radiation area of a radiation delivery device in the radiation treatment system. The at least one block may be situated in a plane different from a plane of the MLC. The at least one block may be made of radiation-impermeable materials (e.g., tungsten, lead, steel alloy, tungsten alloy). Projection of the at least one block may at least cover the end area, thereby shielding at least a portion of the leaking radiation beams within the end area.

By arranging the block(s), radiation beams delivered to a normal portion (e.g., surrounding normal tissues) of the object other than the lesion may be reduced, thereby reducing the relative toxicity of radiation to the surrounding normal tissues. The size of the block(s) may be relatively small, and thus occupy a little space of the radiation treatment system 100. Besides, the weight of the at least one block may be relatively light, and thus cause a little load on the radiation treatment system (e.g., a radiation delivery device of the radiation treatment system). In some cases, by adjusting the size of the at least one block, one or more leaves of the MLC may be designed with a relatively small length and thus the one or more leaves may move more quickly, thereby shortening the time for radiation therapy.

A second aspect of the present disclosure relates to a method for operating a radiation treatment system. A portion of the radiation treatment system may be configured to form an aperture through which a portion of radiation beams is delivered to a treatment region. The portion of the radiation treatment system may include an MLC at least having a first layer of leaves and a second layer of leaves. If the first layer of leaves of the MLC fails to block pathways of leaking radiation beams within a first region other than the treatment region, one or more layers of leaves other than the first layer of leaves and the second layer of leaves of the MLC may be operated to move to form the treatment region with the first layer of leaves. At least a portion of the second layer of leaves may be operated to shield at least a portion of the leaking radiation beams within the first region. If the first layer of leaves blocks pathways of leaking radiation beams within the first region, the one or more layers of leaves and the second layer of leaves may be operated to move to form the treatment region with the first layer of leaves.

By providing the method described above, the MLC may simultaneously form the treatment region and block at least a portion of the leaking radiation beams delivered to the normal portion of the object other than the lesion. In some cases, a boundary of the treatment region may be formed based on a plurality of steps, and at least one width of the plurality of steps may be smaller than the width of each leaf. Thus the resolution (or the fine degree) of the boundary of the treatment region may be improved compared to a boundary of a treatment region formed by the first layer of leaves.

A third aspect of the present disclosure relates to a method for operating a radiation treatment system. A portion of the radiation treatment system may be configured to form an aperture through which a portion of radiation beams is delivered to a treatment region. The portion of the radiation treatment system may include an MLC having at least two layers of leaves and at least one block. If a first layer of leaves of the MLC fails to block pathways of leaking radiation beams within a first region other than the treatment region and the at least one block is able to block at least a portion of leaking radiation beams within the first region, one or more layers of leaves other than the first layer of leaves may be operated to move to form the treatment region with the first layer of leaves. If the first layer of leaves of the MLC fails to block pathways of leaking radiation beams within the first region and the at least one block is unable to block the at least a portion of leaking radiation beams within the first region, at least a portion of the second layer of leaves of the MLC may be operated to move to shield the at least a portion of the radiation beams within the first region. If the first layer of leaves blocks pathways of leaking radiation beams within the first region, the one or more layers of leaves other than the first layer of leaves may be operated to move to form the treatment region with the first layer of leaves.

By providing the method described above, when the at least one block fails to block the at least a portion of leaking radiation beams, at least a portion of leaves of the MLC may be operated to block the at least a portion of leaking radiation beams, thereby ensuring the at least a portion of the leaking radiation beams not to be delivered to the normal portion of the object other than the lesion.

Figure 1:
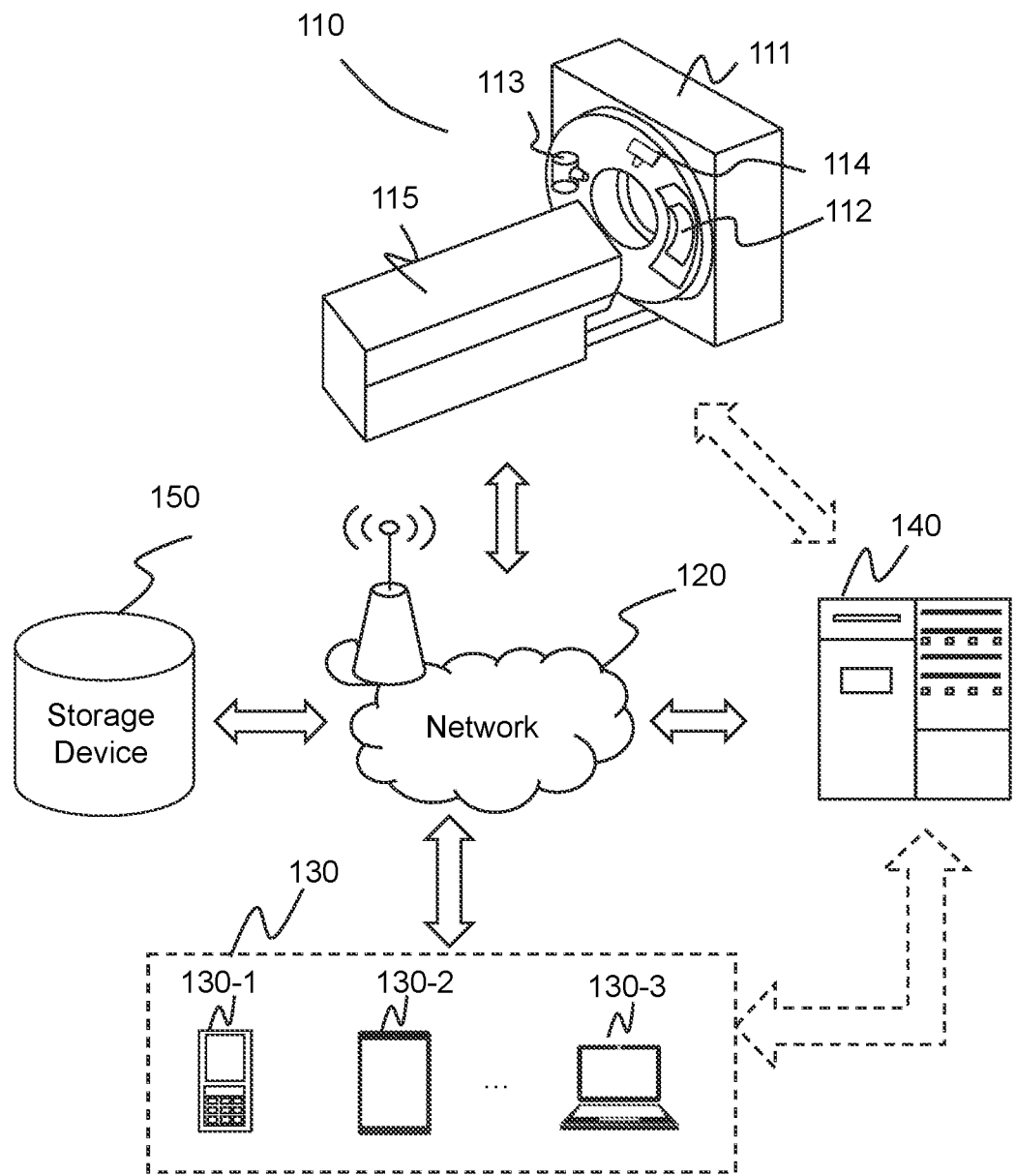
FIG. 1 is a schematic diagram illustrating an exemplary radiation treatment system according to some embodiments of the present disclosure.

FIG. 1 is a schematic diagram illustrating an exemplary radiation treatment system 100 according to some embodiments of the present disclosure. The radiation treatment system 100 may include a radiation delivery device 110, a network 120, one or more terminals 130, a processing device 140, and a storage device 150. The components of the radiation treatment system 100 may be connected in various ways. Mere by way of example, the radiation delivery device 110 may be connected to the processing device 140 through the network 120. As another example, the radiation delivery device 110 may be connected to the processing device 140 directly as indicated by the bi-directional arrow in dotted lines linking the radiation delivery device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

In some embodiments, the radiation delivery device 110 may simultaneously perform imaging and treatment on an object. Mere by way of example, the radiation delivery device 110 may include an imaging assembly, a treatment radiation source (e.g., the first radiation source 114), a gantry 111, and a table 115. The imaging assembly may include a conventional CT, a cone beam CT (CBCT), a helical CT, a multi-slice CT, a PET-CT, or the like, or any combination thereof. The imaging assembly may be configured to generate one or more images before, during or after radiotherapy. As shown in FIG. 1, the imaging assembly may include an imaging radiation source (e.g., the second radiation source 113) and a radiation detector 112 opposite to the second radiation source 113. The gantry 111 may include a rotary ring (not shown in FIG. 1). The rotary ring may be configured to accommodate the second radiation source 113, the radiation detector 112, and the first radiation source 114. In some embodiments, the first radiation source 114 may emit a first beam toward a region (e.g., a tumor) of an object that is placed on the table 115. The second radiation source 113 may emit a second beam toward a second region (e.g., an imaging region) of the object. In some embodiments, the intensity of the first beam may be different from the intensity of the second beam. For example, the energy of the first beam may be several megavolts (MV), this energy being greater than that of the second beam, which may be several kilovolts (kV). The object may be a biological object (e.g., a patient, an animal) or a non-biological object. In the present disclosure, "object" and "subject" are used interchangeably. The radiation detector 112 may be configured to detect radiation emitted from the second radiation source 113. It should be noted that the above descriptions of the radiation delivery device 110 are merely provided for the purposes of illustration, and not intended to limit the scope of the present disclosure. In some embodiments, the imaging assembly in the radiation delivery device 110 may be omitted, and the radiation delivery device 110 may include only one radiation source (e.g., the first radiation source 114) for delivering radiotherapy.

Figure 4A:
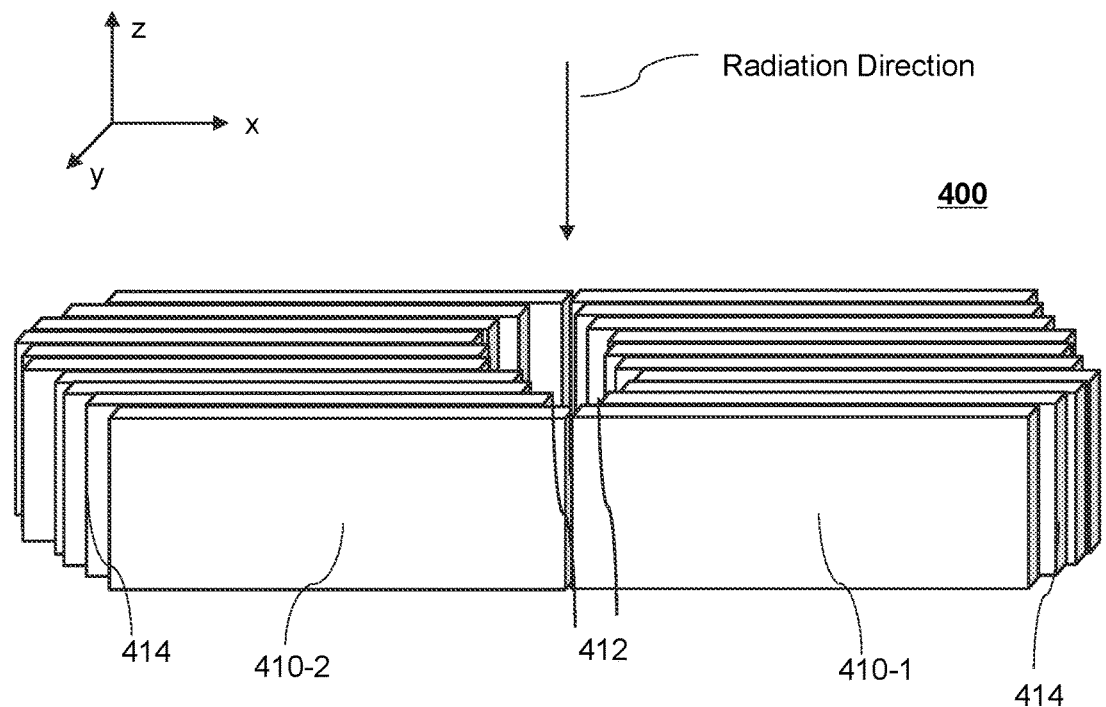
FIG. 4A is a schematic diagram illustrating an exemplary radiation treatment system according to some embodiments of the present disclosure.

In some embodiments, a portion (not shown in FIG. 1) of the radiation delivery device 110 may be configured to collimate radiation beams within a radiation area of the first radiation source 114. In some embodiments, the radiation area may be represented by a rectangle as illustrated in FIGS. 4A-11B. The length of the radiation area may refer to a dimension of the radiation area that is parallel to a leaf moving direction (e.g., a longitudinal direction, the x-direction as illustrated in FIG. 4A). The width of the radiation area may refer to a dimension of the radiation area (e.g., the y-direction as illustrated in FIG. 4A) orthogonal to the direction along which a leaf moves, or referred to as a leaf moving direction (e.g., a longitudinal direction), and a radiation direction (e.g., the z-direction as illustrated in FIG. 4A).

In some embodiments, the portion of the radiation delivery device 110 may form an aperture through which a portion of radiation beams is delivered to a treatment region. In some embodiments, the treatment region may conform to the shape of a lesion. The lesion (e.g., the tumor) of the object may be located at the treatment region for radiotherapy. In some embodiments, a center of the treatment region may be an isocenter of the radiation delivery device 110. As used herein, the isocenter of the radiation delivery device 110 may refer to a point through which central rays of the first radiation source 114 passes during radiotherapy. Thus, the lesion may receive sufficient radiation, and the damage to a normal portion (normal tissues surrounding the lesion) of the object may be reduced during the radiotherapy.

In some current application scenarios, the portion of the radiation delivery device 110 may include a multi-leaf collimator (MLC) having a single layer of leaves. The MLC (or the single layer of leaves) may sometimes fail to block pathways of leaking radiation beams within an end area in the radiation area. As used herein, the end area may form when one or more ends corresponding to one or more leaves of a plurality of leaves included in the MLC within a boundary of the radiation area. Each of the one or more ends may refer to an end of a leaf that is relatively near to the boundary of the radiation area along a longitudinal direction. More detailed descriptions of the leaking radiation beams in the end area with respect to the MLC having the single layer of leaves can be found elsewhere in the present disclosure. See, e.g., FIGS. 4A-4B and the descriptions thereof.

In some current application scenarios, the portion of the radiation delivery device 110 may include an MLC having at least two layers of leaves. The at least two layers of leaves may move along with each another. Accordingly, if a first layer of leaves of the MLC fail to block the leaking radiation beams within a first region other than the treatment region, the MLC (i.e., the at least two layers of leaves) may fail to block the leaking beams within an end area of the radiation area. As used herein, the first region may form when one or more leaves of the first group of the first layer of leaves pass across a first line such that the first region is exposed to allow at least a portion of the first portion of the radiation beams to leak through. Since one or more layers of leaves other than the first layer of leaves may block at least a portion of leaking radiation beams within the first region, the end area may include at least a portion of the first region. More detailed descriptions of the leaking radiation beams in the first region or the end area with respect to the MLC having the at least two layers of leaves can be found elsewhere in the present disclosure. See, e.g., FIGS. 5A-5B and the descriptions thereof.

As described above, the treatment region may conform to the shape of the lesion, the leaking radiation beams within the end area or the at least a portion of the first region may be delivered to the normal portion (e.g., normal tissues surrounding the lesion) of the object, which may cause damage to the normal portion. In order to reduce the damage to the normal portion, the portion of the radiation delivery device 110 should shield at least a portion of leaking radiation beams within the end area (or the at least a portion of the first region). In the present disclosure, ways of shielding the at least a portion of leaking radiation beams within the end area (or the at least a portion of the first region) may include arranging at least one block for the MLC, operating the movement of the MLC, etc. More detailed descriptions can be found elsewhere in the present disclosure. See, e.g., FIGS. 6A-11B and the descriptions thereof.

In some embodiments, each layer of leaves of the MLC described above may include a plurality of leaves. The number or count of the plurality of leaves in the layer of leaves may vary. For illustration purposes, the number of or count of the plurality of leaves in the layer of leaves may include 12, 24, 32, 48, 64, 80, 100, 128, etc. The plurality of leaves may be made of radiation-impermeable materials (e.g., tungsten, lead, steel alloy, tungsten alloy).

In some embodiments, a size of the layer of leaves may relate to one or more of a width of each leaf, a length of each leaf, a thickness of each leaf, etc. The size of the layer of leaves may be a total of sizes of the plurality of leaves. As used herein, the width of a leaf may refer to a dimension of the leaf (e.g., the y-direction as illustrated in FIG. 4A) orthogonal to the direction along which a leaf moves, or referred to as a leaf moving direction (e.g., a longitudinal direction), and a radiation direction (e.g., the z-direction as illustrated in FIG. 4A). The length of a leaf may refer to a dimension of the leaf that is parallel to a leaf moving direction (e.g., a longitudinal direction, the x-direction as illustrated in FIG. 4A). The thickness (or height) of a leaf may refer to a dimension of the leaf along a radiation direction (e.g., the z-direction as illustrated in FIG. 4A). In some embodiments, each leaf of some or all leaves in the layer of leaves may have the same width, the same length, and/or the same thickness.

In some embodiments, a shape or structure of each leaf may be non-limiting. For illustration purposes, a cross-section of each leaf may include a trapezoid, a rectangle, etc. An end of each leaf may have the shape of a rectangle, a square, an arc, etc. In some embodiments, waves or similar geometries may be arranged on leaves so that the plurality of leaves may mutually overlap as viewed from the radiation direction. For illustration purposes, the leaves may include grooves and tongues.

In some embodiments, the layer of leaves may also include a guide rail box, a plurality of driving mechanisms (e.g., a plurality of motors), and a housing (or carriage). In some embodiments, the housing may be configured to accommodate the plurality of leaves. The guide rail box may include a plurality of guide rails. Each guide rail of the plurality of guide rails may be configured to guide a movement of each leaf. The plurality of drive mechanisms may be configured to actuate the plurality of leaves to move along the plurality of guide rails. In some embodiments, at least two leaves of the plurality of leaves may be moveable parallel to each another (e.g., being movable along the x-direction as illustrated in FIG. 4A).

In some embodiments, at least some of the plurality of leaves may be actuated or moved simultaneously. By simultaneously actuating and/or moving at least some of the plurality of leaves, the aperture may form. A portion of radiation beams emitted from the radiation source (e.g., the first radiation source 114) may pass through the aperture, and further travel to the treatment region (e.g., a tumor). In some embodiments, the plurality of drive mechanisms may facilitate the movement of the plurality of leaves such that the layer of leaves can transition between a first aperture shape and a second aperture shape. For illustration purposes, each leaf may be capable of transitioning from a first position to a second position (e.g., from a closed position to a target position).

Figure 4B:
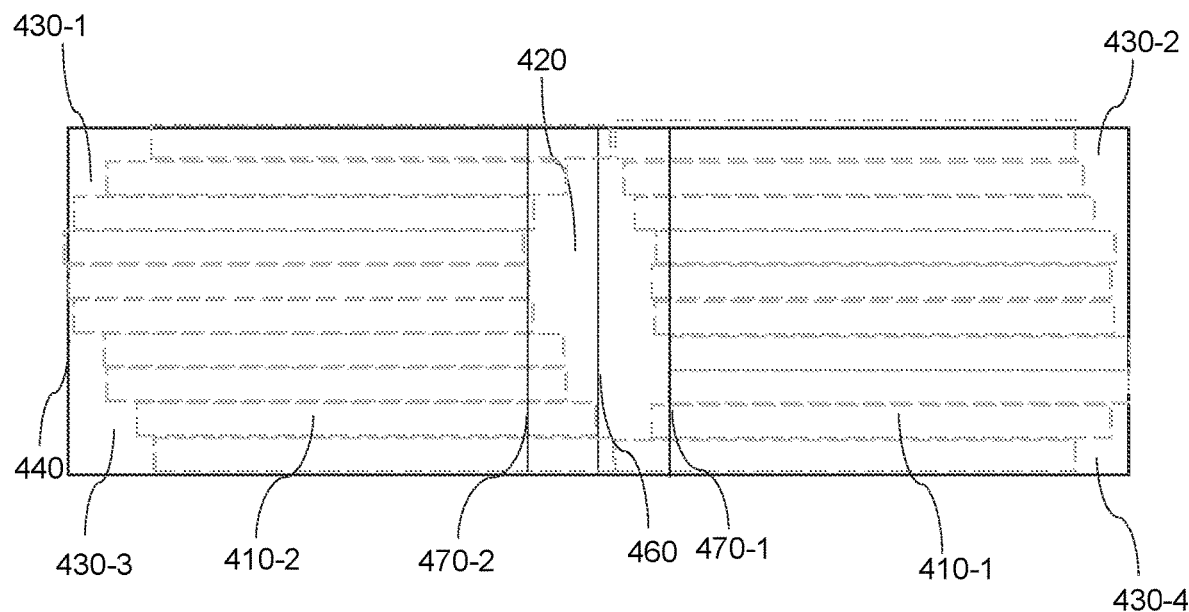
FIG. 4B is a section view illustrating exemplary leaking radiation beams in an end area of a radiation treatment system according to some embodiments of the present disclosure.

A resolution may be used to represent a fine degree of a boundary of a treatment region. The higher the resolution is, the finer the boundary of the treatment region may be. In some embodiments, the resolution may relate to a width of each leave that forms the boundary of the treatment region. For illustration purposes, the boundary of the treatment region may be formed based on a plurality of steps (e.g., as illustrated in FIG. 4B or FIG. 6B), and each step may have the same width as each leave that forms the boundary of the treatment region. In some embodiments, the higher the width of the leave is, the smaller the resolution may be. Generally, the shape of the lesion may be irregular, and the boundary of the treatment region (or the aperture) may be irregular. In order to better conform to the shape of the lesion, the boundary of the treatment region should have a relatively high resolution.

The network 120 may facilitate the exchange of information and/or data. In some embodiments, one or more components of the radiation treatment system 100 (e.g., the radiation delivery device 110, the terminal 130, the processing device 140, or the storage device 150) may send information and/or data to another component(s) in the radiation treatment system 100 via the network 120. For example, the processing device 140 may obtain, via the network 120, a size of a layer of leaves of an MLC from the storage device 150. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Mere by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the radiation treatment system 100 may be connected to the network 120 to exchange data and/or information.

The terminal 130 may include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the radiation delivery device 110. In some embodiments, the terminal 130 may operate the radiation delivery device 110 via a wireless connection. In some embodiments, the terminal 130 may receive information and/or instructions inputted by a user, and send the received information and/or instructions to the radiation delivery device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the radiation delivery device 110, the terminal 130, or the storage device 150. For example, the processing device 140 may determine whether a first region exists. As used herein, the first region may form when one or more leaves of a first group of a first layer of leaves pass across a first line such that the first region is exposed to allow at least a portion of the first portion of the radiation beams to leak through.

The processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the radiation delivery device 110, the terminal 130, and/or the storage device 150 via the network 120. As another example, the processing device 140 may be directly connected to the radiation delivery device 110 (as illustrated by the dashed bidirectional arrow linking the radiation delivery device 110 and the processing device 140 in FIG. 1), the terminal 130 (as illustrated by the dashed bidirectional arrow linking the terminal 130 and the processing device 140 in FIG. 1), and/or the storage device 150, to access information and/or data. In some embodiments, the processing device 140 may be implemented on a cloud platform. Mere by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Mere by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the radiation treatment system 100 (e.g., the terminal 130, the processing device 140). One or more components of the radiation treatment system 100 may access the data or instructions stored in the storage device 150 via the network 120. In some embodiments, the storage device 150 may be directly connected to or communicate with one or more components of the radiation treatment system 100 (e.g., the terminal 130, the processing device 140). In some embodiments, the storage device 150 may be part of the processing device 140.

FIG. 2 is a schematic diagram illustrating exemplary hardware and/or software components of a computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the radiation delivery device 110, the terminal 130, the storage device 150, and/or any other component of the radiation treatment system 100. For example, the processor 210 may determine whether a first region exists. As used herein, the first region may form when one or more leaves of a first group of a first layer of leaves pass across a first line such that the first region is exposed to allow at least a portion of the first portion of the radiation beams to leak through. The processor 210 may cause at least a portion of a second layer of leaves of the MLC to move to shield at least a portion of the leaking radiation beams within the first region. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the radiation delivery device 110, the terminal 130, the storage device 150, or any other component of the radiation treatment system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the radiation delivery device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
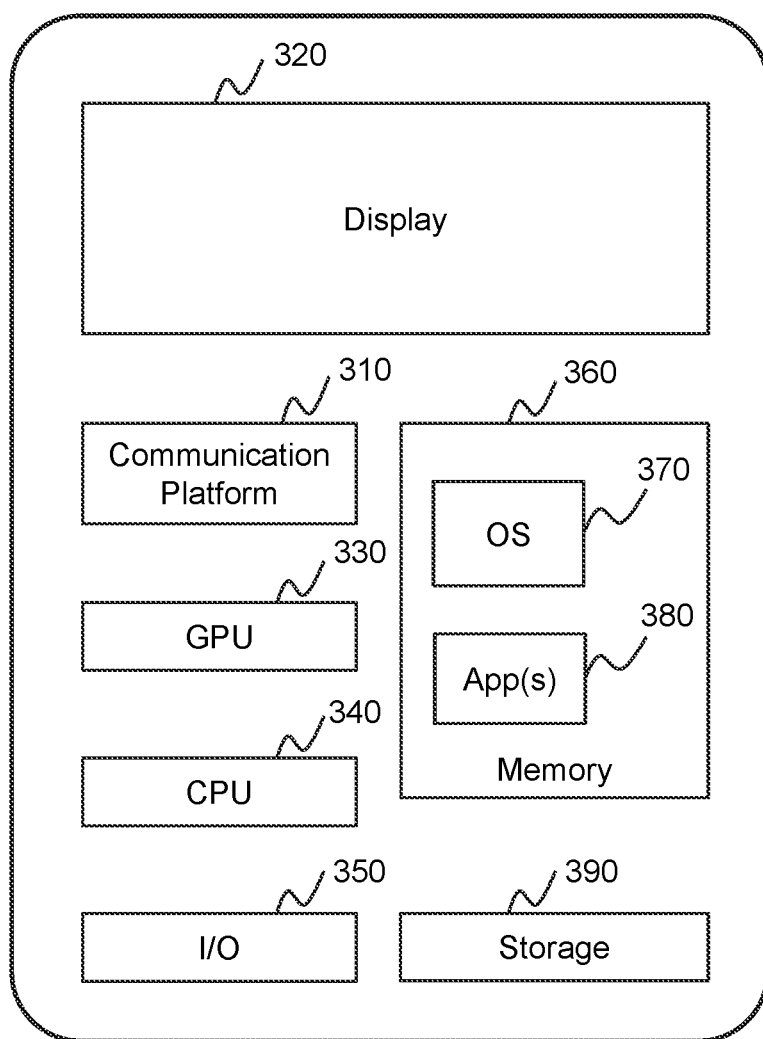
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation treatment system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to shield at least a portion of leaking radiation beams in a region other than a treatment region as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

FIG. 4A is a schematic diagram illustrating an exemplary radiation treatment system 400 according to some embodiments of the present disclosure. FIG.4B is a section view illustrating exemplary leaking radiation beams in an end area of the radiation treatment system 400 according to some embodiments of the present disclosure. It should be noted that FIGS. 4A-4B only illustrate a portion of components of the radiation treatment system 400. The portion of components of the radiation treatment system 400 may be configured to form an aperture through which a portion of radiation beams is delivered to a treatment region. The radiation treatment system 400 may also include an imaging assembly (e.g., CT, CBCT), a treatment radiation source (e.g., the first radiation source 114), a gantry (e.g., the gantry 111), a table (e.g., the table 115), etc.

As illustrated in FIGS. 4A-4B, the radiation treatment system 400 may include an MLC having single layer of leaves. The layer of leaves may be an example of the layer of leaves described in FIG. 1. The MLC (or the layer of leaves) may include two opposing groups of leaves, i.e., a first group of leaves 410-1 (also referred to as "leaves 410-1") and a second group of leaves 410-2 (also referred to as "leaves 410-2"). A cross-section of each leaf may be rectangular. Each leaf may include a first end (also referred to as "front end") and a second end (also referred to as "rear end") located at the ends of the leaf along the longitudinal direction of the leaf (e.g., along the x-direction). The front end 412 of a leaf may refer to the end of the leaf that faces an end of another leaf and the rear end 414 may refer to the other end of the leaf. As illustrated in FIG. 4B, projection of the leaves of the MLC may be represented by rectangles with dotted lines.

As illustrated in FIG. 4B, a rectangle 440 may represent a radiation area (e.g., the maximum of the radiation area of the first radiation source 114). Similar to the radiation treatment system 100 described above, the radiation treatment system 400 may form the aperture through which a portion of radiation beams is delivered to the treatment region. A region formed by front ends of the leaves 410-1 and the leaves 410-2 may constitute the treatment region, e.g., a region 420 as illustrated in FIG. 4B. In some embodiments, a lesion (e.g., the tumor) of the object may be located at the region 420 for radiotherapy.

As described in FIG. 1, the region 420 may conform to the shape of the lesion. In order to reduce the damage of radiation beams to a normal portion (e.g., the normal tissues) of the object, radiation beams should be blocked to deliver to a region other than the region 420. However, as illustrated in FIG. 4B, except the region 420, the MLC may only shield radiation beams within a region covered by the rectangles with dotted lines, and fail to block pathways of leaking radiation beams in one or more regions, e.g., a region 430-1, a region 430-2, a region 430-3, and a region 430-4 (also collectively referred to as "end area").

As illustrated in FIG. 4B, the region 430-1 and the region 430-3 may be in the left side of the region 420 (i.e., the radiation area). The region 430-2 and the region 430-4 may be in the right side of the region 420. It should be noted the end area constituted by the region 430-1, the region 430-2, the region 430-3, and the region 430-4 may be exemplary. The end area may also include at least one region in the left side and/or at least one region in the right side (not shown in FIG. 4B). For example, the end area may include two regions in the left side. As another example, the end area may include two regions in the right side. As a further example, the end area may include a region in the right side and a region in the left side.

As illustrated in FIG. 4B, solid line 460 may represent a centerline of the rectangle 440. Each leave may have the same length, and the length may be smaller than a half of the length of the rectangle 440. A distance between solid line 470-1 (also referred to as "first line") and a right edge of the rectangle 440 may be the same as the length of the leave. The region 430-2 and the region 430-4 may form by one or more of the leaves 410-1 passing across the solid line 470-1. Similarly, a distance between solid line 470-2 (also referred to as "second line") and a left edge of the rectangle 440 may be the same as the length of the leave. The region 430-1 and the region 430-3 may form by one or more of the leaves 410-2 passing the solid line 470-2. It should be noted that the first line and the second line may interchange. For example, solid line 470-1 may be determined as the second line, and solid line 470-2 may be determined as the first line.

Each boundary of the region 430-1, the region 430-2, the region 430-3 and the region 430-4 may be determined based on one or more second ends of the one or more leaves of the first group of leaves and a first portion of a boundary of the radiation area. As illustrated in FIG. 4B, the boundary of the region 430-1 may be determined based on second ends of three leaves in the upper side and two edges (i.e., the left edge, an upper edge) of the radiation area. The boundary of the region 430-2 may be determined based on second ends of six leaves in the upper side and two edges (i.e., the right edge, the upper edge) of the radiation area. The boundary of the region 430-3 may be determined based on second ends of five leaves in the lower side and two edges (i.e., the left edge, a lower edge) of the radiation area. The boundary of the region 430-4 may be determined based on second ends of two leaves in the lower side and two edges (i.e., the right edge, the lower edge) of the radiation area.

Figure 5A:
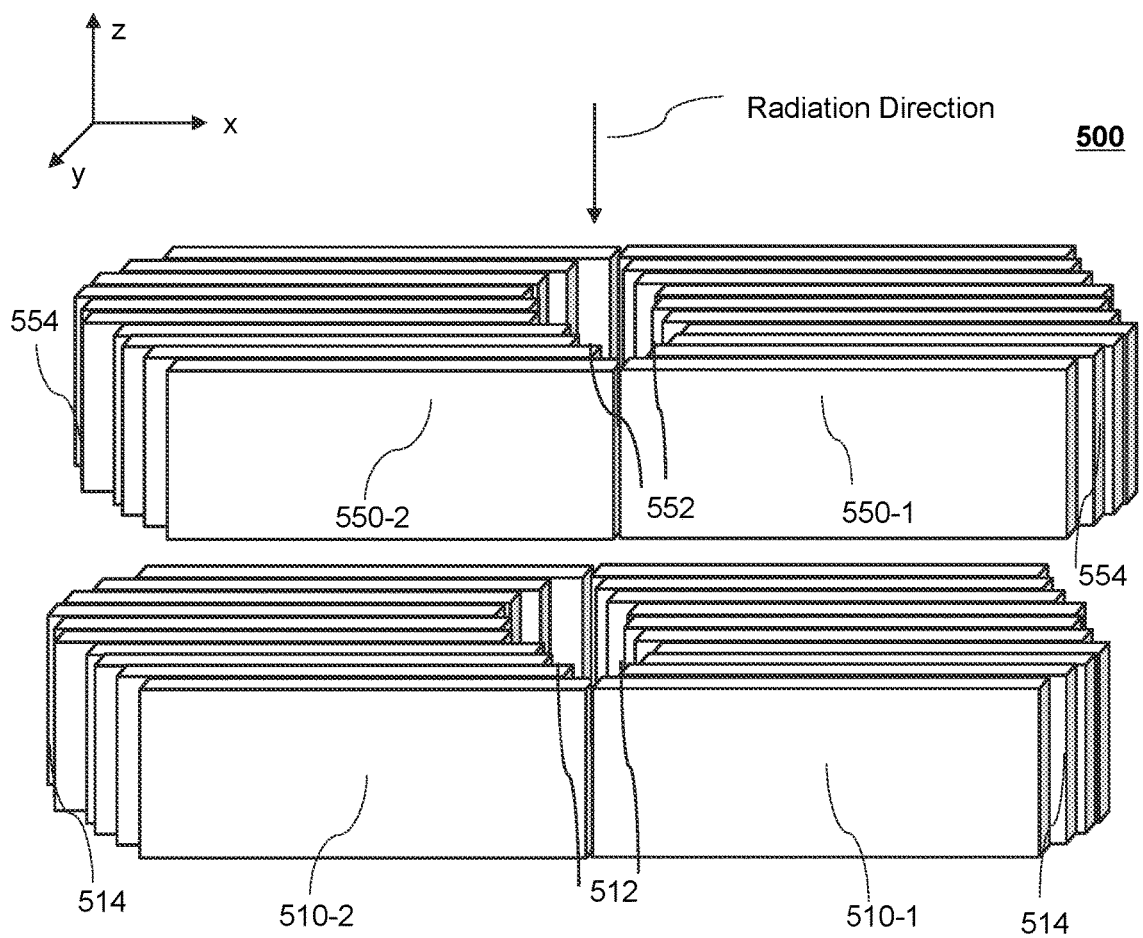
FIG. 5A is a schematic diagram illustrating an exemplary radiation treatment system according to some embodiments of the present disclosure.
Figure 5B:
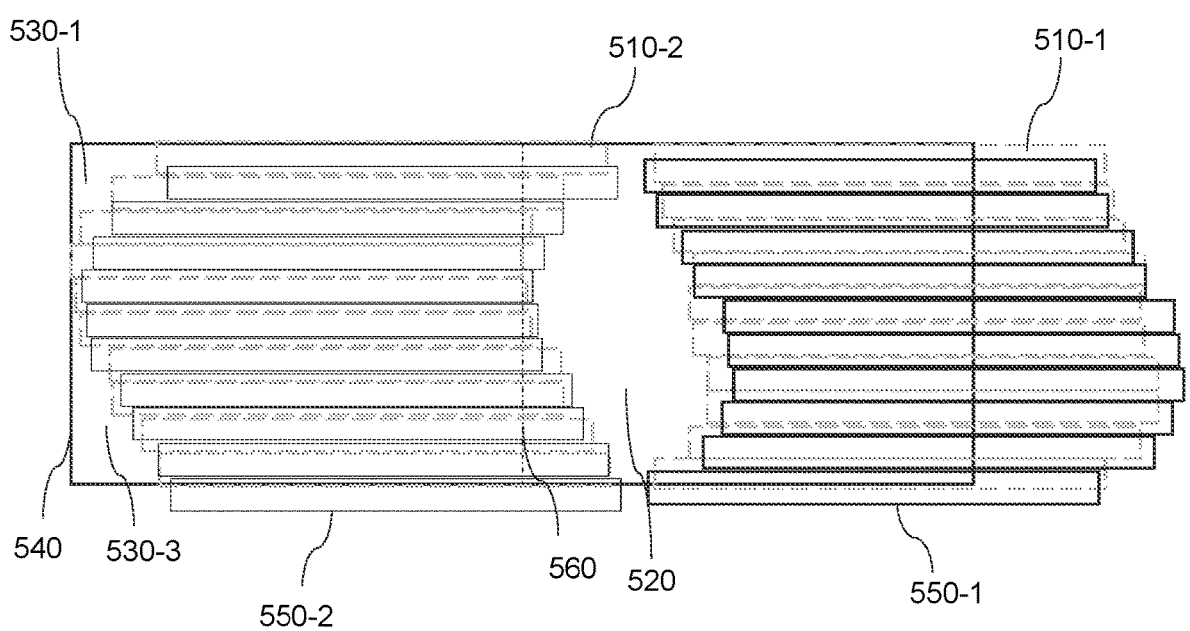
FIG. 5B is a section view illustrating exemplary leaking radiation beams in an end area of a radiation treatment system according to some embodiments of the present disclosure.

FIG. 5A is a schematic diagram illustrating an exemplary radiation treatment system 500 according to some embodiments of the present disclosure. FIG. 5B is a section view illustrating exemplary leaking radiation beams in an end area of the radiation treatment system 500 according to some embodiments of the present disclosure. It should be noted that FIGS. 5A-5B only illustrate a portion of components of the radiation treatment system 500. The portion of components of the radiation treatment system 500 may be configured to form an aperture through which a portion of radiation beams is delivered to a treatment region. The radiation treatment system 500 may also include an imaging assembly (e.g., CT, CBCT), a treatment radiation source (e.g., the first radiation source 114), a gantry (e.g., the gantry 111), a table (e.g., the table 115), etc.

The radiation treatment system 500 may include an MLC having two layers of leaves. Each of the two layers of leaves may be similar to or the same as the layer of leaves described in FIG. 1. As illustrated in FIGS. 5A-5B, a first layer of leaves of the MLC may include a first group of leaves 510-1 (also referred to as "leaves 510-1") and a second group of leaves 510-2 (also referred to as "leaves 510-2"). A cross-section of each leaf may be rectangular. Each leaf may include a first end (also referred to as "front end") and a second end (also referred to as "rear end") located at the ends of the leaf along the longitudinal direction of the leaf (e.g., along the x-direction). The front end 512 of a leaf may refer to the end of the leaf that faces an end of another leaf and the rear end 514 may refer to the other end of the leaf. As illustrated in FIG. 5B, projection of the leaves of the first layer of leaves may be represented by rectangles with dotted lines.

A second layer of leaves of the MLC may be situated above the first layer of leaves. The second layer of leaves may include a first group of leaves 550-1 (also referred to as "leaves 550-1") and a second group of leaves 550-2 (also referred to as "leaves 550-2"). A cross-section of each leaf may be rectangular. Each leaf may include a first end (also referred to as "front end") and a second end (also referred to as "rear end") located at the ends of the leaf along the longitudinal direction of the leaf (e.g., along the x-direction). The front end 552 of a leaf may refer to the end of the leaf that faces an end of another leaf and the rear end 554 may refer to the other end of the leaf. As illustrated in FIG. 5B, projection of the leaves of the second layer of leaves may be represented by rectangles with solid lines.

As illustrated in FIG. 5B, a rectangle 540 may represent a radiation area (e.g., the maximum of the radiation area of the first radiation source 114). Similar to the radiation treatment system 100 described above, the radiation treatment system 500 may form the aperture through which a portion of radiation beams is delivered to the treatment region. A region formed by front ends of the leaves 510-1, the leaves 510-2, the leaves 550-1, and the leaves 550-2 may constitute the treatment region, e.g., a region 520 as illustrated in FIG. 5B. In some embodiments, a lesion (e.g., the tumor) of the object may be located at the region 520 for radiotherapy.

As described in FIG. 1, the region 520 may conform to the shape of the lesion. In order to reduce the damage of radiation beams to a normal portion (e.g., the normal tissues) of the object, radiation beams should be blocked to deliver to a region other than the region 520. However, as illustrated in FIG. 5B, except the region 520, the MLC may only shield radiation beams within a region covered by the rectangles with dotted lines and the rectangles with solid lines, and fail to block pathways of leaking radiation beams in one or more regions, e.g., a region 530-1 and a region 530-3 (also collectively referred to as "end area").

The region 530-1 and the region 530-3 may be in the left side of the region 520 (i.e., the radiation area). It should be noted that the end area constituted by the region 530-1 and the region 530-3 may be exemplary. The end area may also include at least region in the right side of the radiation area and/or at least one region in the left side and at least one region in the right side (not shown in FIG. 4B), etc. For example, the end area may include two regions in the left side. As another example, the end area may include two regions in the right side. As a further example, the end area may include a region in the right side and a region in the left side.

As illustrated in FIG. 5B, dotted line 560 may represent a centerline of the rectangle 540. Each leave may have the same length, and the length may be equal to a half of the length of the rectangle 540. The region 530-1 and the region 530-3 may form by one or more of the leaves 510-2 and/or one or more of the leaves 550-2 passing across the dotted line 560. Similarly, when one or more of the leaves 510-1 and/or one or more of the leaves 550-1 pass across the dotted line 560 (not shown in FIG. 5B), the MLC may fail to block leaking radiation beam in at least one region within the radiation area.

In some embodiments, in order to solve the problems (the leaking radiation beams in the end area) described in FIG. 1, and FIGS. 4A-5B, embodiments of the present disclosure may provide a radiation treatment system. The radiation treatment system may at least include an MLC having at least one layer of leaves and at least one block. Each of the at least one layer of leaves may be an example of the layer of leaves described in FIG. 1. Each of the layer of leaves may include two opposing groups of leaves, i.e., a first group of leaves and a second group of leaves 410-2. At least a portion of the leaves may be movable to block pathways of a first portion of radiation beams within a radiation area. A second portion of the radiation beams may be incident at a treatment region of the radiation treatment system 100. As described above, the treatment region should conform to the shape of the lesion, and the lesion (e.g., the tumor) of the object may be located at the treatment region for radiotherapy. Thus the first portion and/or the second portion of radiation beams may relate to the shape of the lesion. For illustration purposes, the first portion of radiation beams may include at least a portion of radiation beams other than a portion (e.g., the second portion) of radiation beams within the treatment region.

In some embodiments, the at least one block may be made of radiation impermeable materials (e.g., tungsten, lead, steel alloy, tungsten alloy). The at least one block may be arranged along a direction of the radiation beams towards the object. The at least one block may be configured to shield at least a portion of leaking radiation beams in a region (e.g., an end area) other than a treatment region. In some embodiments, projection of the at least one block may at least cover the end area thereby blocking the at least a portion of leaking radiation beams within the end area. Thus, the at least a portion of leaking radiation beams may fail to project on the object, thereby reducing damage of the leaking radiation beams on a normal portion of the object.

In some embodiments, each of the at least one layer of leaves may be similar to or the same as the layer of leaves described in FIG. 1. Each of the at least one layer of leaves may include a first group of leaves and a second group of leaves. As described above, the MLC (or the at least one layer of leaves) may be configured to form an aperture through which a portion of radiation beams is delivered to a treatment region. In some embodiments, the treatment region may conform to the shape of the lesion, and the lesion (e.g., the tumor) of the object may be located at the treatment region for radiotherapy.

The aperture (or the treatment region) may change according to the shape of the lesion of the object. In some embodiments, the aperture may change by moving at least one leaf of the first group of leaves or at least one leaf of the second group of leaves from at least one first position (e.g., forming a first aperture) to at least one second position (e.g., forming a second aperture).

Similar to the radiation treatment system described FIGS. 4A-5B, the end area may form in the radiation area when the at least one leaf of the MLC moves so that the MLC may fail to block pathways of leaking radiation beams in the end area. In some embodiments, when one or more second ends of one or more leaves of the at least one leave are within a boundary of the radiation area, the MLC may fail to block the pathways of leaking radiation beams in the end area. Similar to the treatment region, an area of the end area may change when the at least one leaf of the first group of leaves or at least one leaf of the second group of leaves moves from the at least one first position to the at least one second position.

In some embodiments, the end area may include a first section (e.g., the region 430-2 and the region 430-4 as illustrated in FIG. 4B) that forms when one or more leaves of the first group of at least one of the at least one layer of leaves pass across a first line such that the first section is exposed to allow at least a portion of the first portion of the radiation beams to leak through. That is, one or more second ends (or rear ends) of the one or more leaves may be within the boundary of the radiation area. The boundary of the first section may be determined similar to or the same as the end area described FIGS. 4A-4B, and not repeated here.

In some embodiments, the first line may relate to a length of each of the first group of leaves and the length of the radiation area. For illustration purposes, the length of each of the first group of leaves may be the same, and a distance between a first edge of the radiation area and the first line may be equal to a length of each of the first group of leaves. The first edge may refer to an edge of the boundary of the radiation area that is relatively far from the second group of leaves along a longitudinal direction. In some embodiments, when the length of each of the first group of leaves may be half of the length of the radiation area, the first line may be a centerline (e.g., the dotted line 560 as illustrated in FIG. 5B) of the radiation area. In some embodiments, when the length of each of the first group of leaves may be smaller than the half of the length of the radiation area, the first line may be a line (e.g. the solid line 470-1 as illustrated in FIG. 4B) parallel with the centerline of the radiation area.

In some embodiments, the end area may include a second section (e.g., the region 430-1 and the region 430-3 as illustrated in FIG. 4B) that forms when one or more leaves of the second group of at least one of the at least one layer of leaves pass across a second line such that the second section is exposed to allow at least a portion of the first portion of the radiation beams to leak through. That is, one or more second ends (or rear ends) of the one or more leaves may be within the boundary of the radiation area. The boundary of the end area may be determined similar to or the same as the end area described FIGS. 4A-4B, and not repeated here. In some embodiments, similar to the first line, the second line may relate to a length of each of the second group of leaves. For illustration purposes, the length of each of the second group of leaves may be the same, and a distance between a second edge of the radiation area and the second line may equal to a length of each of the second group of leaves. The second edge may refer to an edge of the boundary of the radiation area that is relatively far from the first group of leaves along a longitudinal direction. In some embodiments, when the length of each of the second group of leaves may be half of the length of the radiation area, the second line may be a centerline (e.g., the dotted line 560 as illustrated in FIG. 5B) of the radiation area. In some embodiments, when the length of each of the first group of leaves may be smaller than the half of the length of the radiation area, the second line may be a line (e.g. the solid line 470-2 as illustrated in FIG. 4B) parallel with the centerline of the radiation area.

In some embodiments, the size (e.g., a width, a length, a thickness (or height)) of each of the at least one block may relate to a first reference distance that at least one leaf of the first group of leaves is allowed to move, a second reference distance that at least one leaf of the second group of leaves is allowed to move, a size of each of the at least one layer of leaves, a length of at least one leaf of the first group of leaves, or a length of at least one leaf of the second group of leaves, or the like, or any combination thereof. As used herein, the width of a block may refer to a dimension of the block (e.g., the y-direction as illustrated in FIG. 4A) orthogonal to the direction along which a leaf moves, or referred to as a leaf moving direction (e.g., a longitudinal direction), and a radiation direction (e.g., the z-direction as illustrated in FIG. 4A). The length of a block may refer to a dimension of the block that is parallel to a leaf moving direction (e.g., a longitudinal direction, the x-direction as illustrated in FIG. 4A). The thickness (or height) of a block may refer to a dimension of the block along a radiation direction (e.g., the z-direction as illustrated in FIG. 4A).

In some embodiments, the first reference distance and the second reference distance may be the same. The length of the at least one leaf of the first group of leaves and the length of at least one leaf of the second group of leaves may be the same. In some embodiments, if the length of the at least one leaf of the first group of leaves or the length of at least one leaf of the second group of leaves remains the same, the larger the first reference distance or the second reference distance is, the larger the length of each of the at least one block may be. In some embodiments, if the first reference distance or the second reference distance remains the same, the larger length of the at least one leaf of the first group of leaves or the length of at least one leaf of the second group of leaves is, the smaller the length of each of the at least one block may be.

As used herein, the size of each of the at least one layer of leaves may refer to a length of the layer of leaves and a width of the layer of leaves in two dimensions. In some embodiments, the length of the layer of leaves may be equal to the length of each leaf. The width of the layer of leaves may include a total of width of the first group of leaves or the second group of leaves. In some embodiments, the larger the width of each of the at least one layer of leaves, the larger the width of each of the at least one block may be. In some embodiments, each layer of leaves may have the same thickness. A space for holding the MLC and the at least one block may be unchangeable. The greater the number or the count of the layers of leaves in the MLC, the smaller the thickness of the at least one block may be.

In some embodiments, the size of the at least one block may also relate to a mounting mode of the at least one block. In a first mounting mode, the at least one block may be moveable along with the MLC. A region that the at least one block shields may change with the movement of the MLC. In some embodiments, the at least one block may move to a position when projection of the at least one block at least covers the end area. In a second mounting mode, the at least one block may be fixed. A region that the at least one block shields may be fixed. Projection of the at least one block may at least cover the end area during the movement of the MLC. In some embodiments, the projection of the at least one block may also partially overlap the MLC during the movement of the MLC. In some embodiments, a size of the at least one block using the first mounting mode may be relatively smaller than the size of the at least one block using the second mounting mode.

In some embodiments, the at least one block may be retractable. For illustration purposes, if the end area does not exist, the at least one block may retract back. If the end area exists, the at least one block may retract out. In some embodiments, a first portion of the at least one block may be moveable or retractable. A second portion of the at least one block may be fixed.

In some embodiments, the shape and/the size of the at least one block may be determined based on empirical data or an algorithm, e.g., a Monte Carlo simulation algorithm, etc. The shape and size of the at least one block may be non-limiting if the at least one block blocks the at least a portion of leaking radiation beams within the end area. For illustration purposes, the shape of the at least one block may include rectangle, square, circle, polygon, trapezoid, etc. The size of the at least one block may be large enough to block the at least a portion of leaking radiation beams within the end area. In some embodiments, when one or more leaves of the first group of leaves passes across the first reference distance or one or more leaves of the first group of leaves passes across the second reference distance and thus forms an end area, the at least one block may shield at least a portion of leaking radiation beam within the end area.

By arranging the block(s), radiation beams delivered to a normal portion (e.g., surrounding normal tissues) of the object other than the lesion may be reduced, thereby reducing the relative toxicity of radiation to the surrounding normal tissues. The projection of the at least one block may at least cover the end area, and the size of the block(s) may be relatively small, and thus occupy a little space of the radiation treatment system 100. Besides, the weight of the at least one block may be relatively light, and thus cause a little load on the radiation treatment system (e.g., a radiation delivery device of the radiation treatment system). In some cases, by adjusting a size of the at least one block, each leaf of the MLC may be designed with a relatively small length and thus the leaf may move more quickly, thereby shortening the time for radiation therapy.

In some embodiments, the present disclosure may provide a radiation treatment system. The radiation treatment system may include the MLC, the at least one block described above and a radiation source. The radiation source may emit radiation beams. As used herein, the radiation source may be similar to or the same as the first radiation source 114 as described in FIG. 1.

Figure 6A:
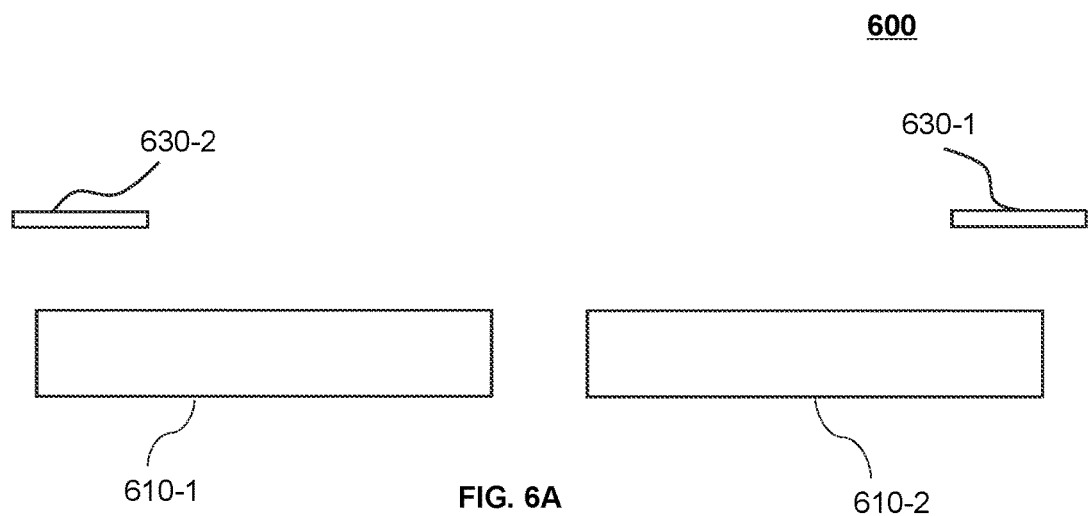
FIGS. 6A-6B are section views illustrating an exemplary radiation treatment system according to some embodiments of the present disclosure.
Figure 6B:
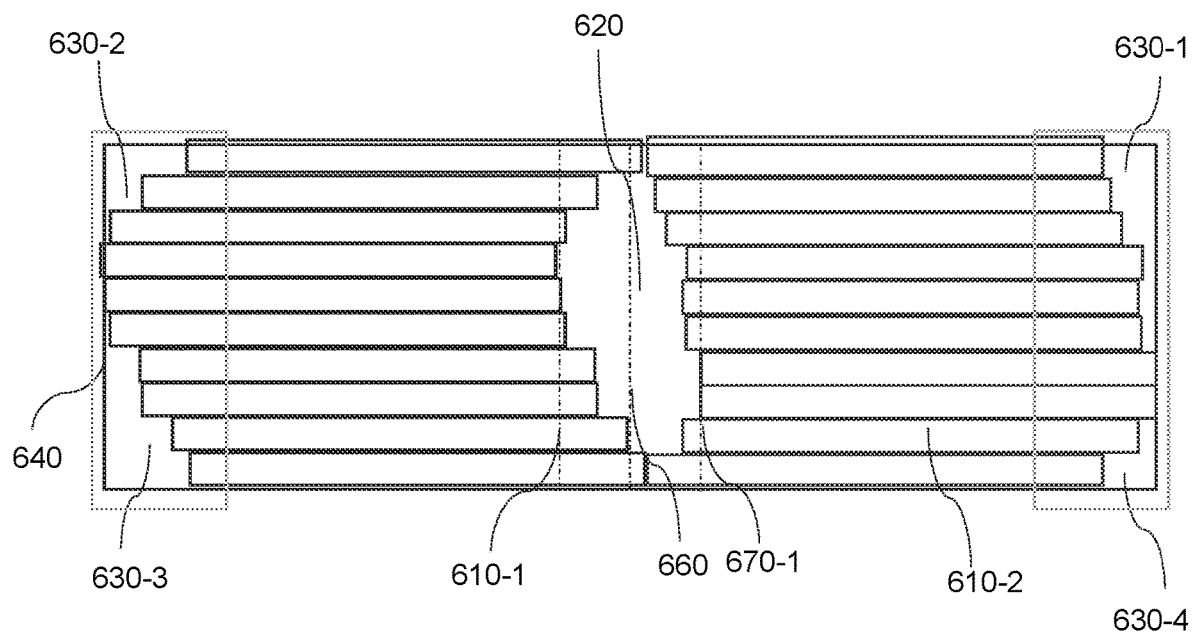

FIGS. 6A and 6B are section views illustrating an exemplary radiation treatment system 600 according to some embodiments of the present disclosure. The radiation treatment system 600 may be an example of the radiation treatment system described above. It should be noted that FIGS. 6A-6B only illustrate a portion of components of the radiation treatment system 600. The portion of components of the radiation treatment system 600 may be configured to form an aperture through which a portion of radiation beams is delivered to a treatment region. The radiation treatment system 600 may also include an imaging assembly (e.g., CT, CBCT), a treatment radiation source (e.g., the first radiation source 114), a gantry (e.g., the gantry 111), a table (e.g., the table 115), etc.

The radiation treatment system 600 may include an MLC having a single layer of leaves, a first block 630-1, and a second block 630-2. The MLC (or the layer of leaves) may include a first group of leaves 610-1 (also referred to as "leaves 610-1") and a second group of leaves 610-2 (also referred to as leaves 610-2"). The first block 630-1 may be situated above the leaves 610-1. The second block 630-2 may be situated above the leaves 610-2.

As illustrated in FIG. 6B, the MLC may form an aperture through which a portion of radiation beams is delivered to a treatment region. A region formed by front ends of the leaves 610-1 and the leaves 610-2 may constitute the treatment region, e.g., a region 620 as illustrated in FIG. 6B. A rectangle 640 may represent a radiation area (a maximum of the radiation area of the first radiation source 114). Radiation beams within a region other than the treatment region may be shielded by the MLC and the two blocks (i.e., the first block 630-1, the second block 630-2).

Figure 7:
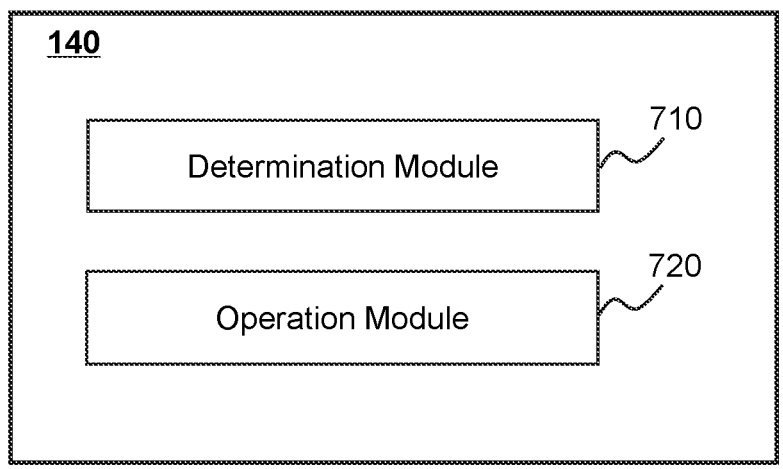
FIG. 7 is a block diagram illustrating an exemplary processing device according to some embodiments of the present disclosure.

FIG. 7 is a block diagram illustrating an exemplary processing device 140 according to some embodiments of the present disclosure. The processing device 140 may be implemented on the computing device 200 (e.g., the processor 210) as illustrated in FIG. 2 or the CPU 340 as illustrated in FIG. 3. The processing device 140 may include a determination module 710 and an operation module 720.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

The determination module 710 may be configured to determine whether a first region exists. As described above, the first region may form when one or more leaves of the first group of the first layer of leaves pass across a first line such that the first region is exposed to allow at least a portion of the first portion of the radiation beams to leak through. More detailed descriptions of the first line can be found elsewhere in the present disclosure. See, e.g., FIGS. 4A-6B. If the radiation treatment system only includes the MLC, in response to a determination that the first region exists, the operation module 720 may cause one or more leaves of a second layer of leaves of the MLC to move to shield at least a portion of leaking radiation beams within the first region. In response to a determination that the first region does not exist, the operation module 720 may cause the second layer of leaves to move to block a part of the second portion of the radiation beams. In some embodiments, the operation module 720 may cause one or more leaves of the second layer of leaves to move to block the part of the second portion of the radiation beams. In some embodiments, the operation module 720 may cause all leaves of the second layer of leaves to move to block the part of the second portion of the radiation beams. In some embodiments, the operation module 720 may cause the one or more leaves or all leaves of the second layer of leaves to move along with the first layer of leaves.

If the radiation treatment system also includes at least one block similar to or the same as the at least one block described in FIGS. 6A-6B, if the at least one block is fixed, projection of the at least one block may shield at least a portion of leaking radiation beam in the first region. In response to a determination that the first region exists, the operation module 720 may cause one or more leaves or all leaves of the second layer of leaves to move to block a part of the second portion of the radiation beams. In some embodiments, the operation module 720 may cause the one or more leaves or all leaves of the second layer of leaves to move along with the first layer of leaves. If the at least one block is moveable, in response to a determination that the first region exists, the operation module 720 may determine whether the at least one block is able to move. In response to a determination that the at least one block is able to move, the operation module 720 may cause the at least one block to shield the at least a portion of leaking radiation beam in the first region, and cause one or more leaves or all leaves of the second layer of leaves to move to block a part of the second portion of the radiation beams. In some embodiments, the operation module 720 may cause the one or more leaves or all leaves of the second layer of leaves to move along with the first layer of leaves. In response to a determination that the at least one block is unable to move, the operation module 720 may cause one or more leaves of the second layer of leaves to shield the at least a portion of leaking radiation beam in the first region.

In some embodiments, a radiation treatment system may at least include an MLC having at least two layers of leaves. In some embodiments, the at least two layers of leaves may be arranged stacked one above another. In some embodiments, the at least two layers of leaves may be arranged in parallel and have an offset such that each leaf in a first layer of leaves may be offset from a leaf in another layer of leaves, e.g., in the longitudinal direction. At least a portion of the leaves may be movable to block pathways of a first portion of radiation beams within a radiation area. A second portion of the radiation beams may be incident at a treatment region of the radiation treatment system 100. As described above, the treatment region should conform to the shape of the lesion. The lesion (e.g., the tumor) of the object may be located at the treatment region for radiotherapy. Thus the first portion and/or the second portion of radiation beams may relate to the shape of the lesion. For illustration purposes, the first portion of radiation beams may include at least a portion of radiation beams other than a portion (e.g., the second portion) of radiation beams within the treatment region. Each of the at least two layers of leaves may be similar to or the same as the layer of leaves described in FIG. 1.

Figure 8:
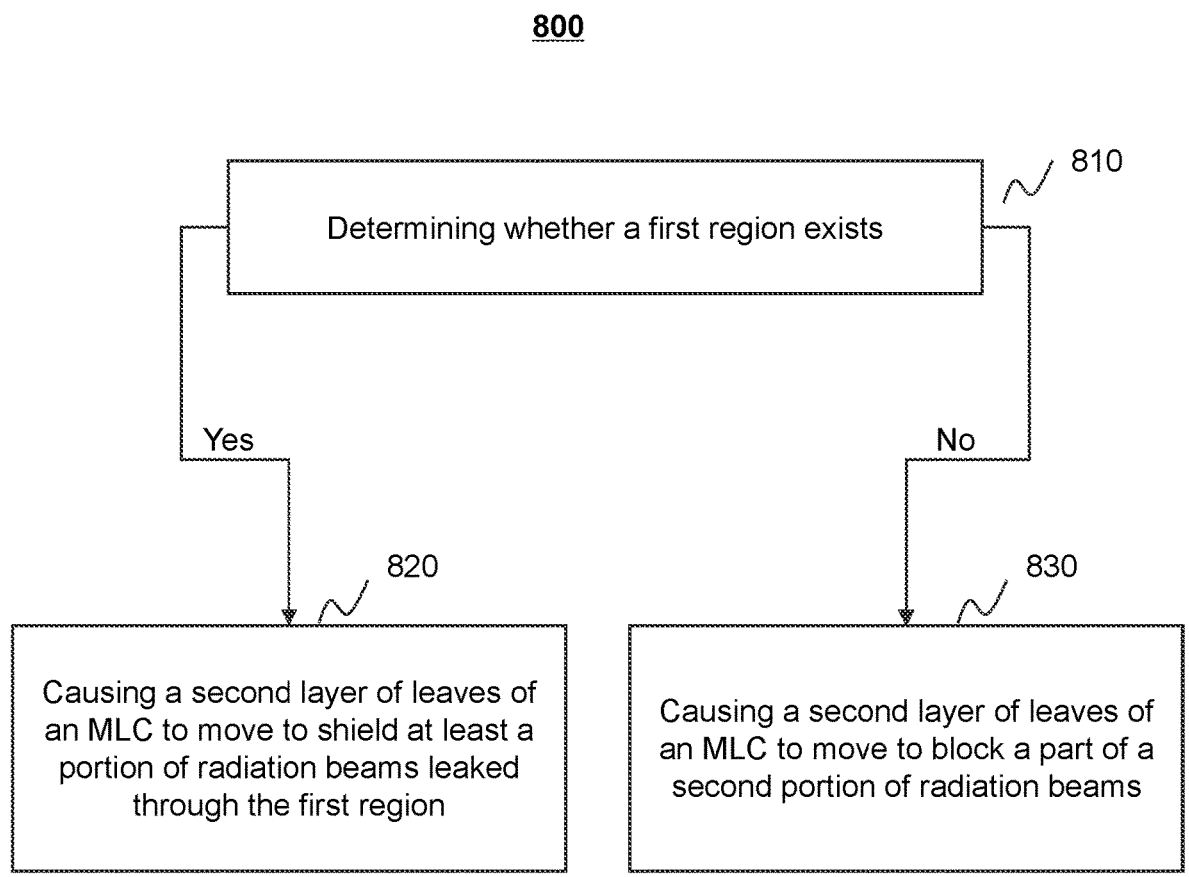
FIG. 8 is a flowchart illustrating an exemplary process for operating a radiation treatment system according to some embodiments of the present disclosure.

FIG. 8 is a flowchart illustrating an exemplary process 800 for operating the radiation treatment system according to some embodiments of the present disclosure. The process 800 may be implemented in the radiation treatment system 100 illustrated in FIG. 1. For example, the process 800 may be stored in the storage device 150 and/or the storage 220 in the form of instructions (e.g., an application), and invoked and/or executed by the processing device 140 (e.g., the processor 210 illustrated in FIG. 2, the CPU 340 as illustrated in FIG. 3, or one or more modules in the processing device 140 illustrated in FIG. 7). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, the processing device 140 (e.g., the determination module 710) may determine whether a first region exists. As described above, the first region may form when one or more leaves of the first group of the first layer of leaves pass across a first line such that the first region is exposed to allow at least a portion of the first portion of the radiation beams to leak through. More detailed descriptions of the first line can be found elsewhere in the present disclosure. See, e.g., FIGS. 4A-6B.

The processing device 140 (e.g., the operation module 720) may cause a second layer of leaves of the MLC to operate based on a determination result in 810. For illustration purposes, the MLC may include the first layer of leaves and the second layer of leaves. In response to a determination that the first region exists, the processing device 140 may cause the second layer of leaves of the MLC to move to shield at least a portion of leaking radiation beams within the first region in 820, which may reduce the damage of the leaking radiation beams within the first region to the normal tissues of the object. In some embodiments, the processing device 140 may transmit an instruction for shielding the at least a portion of leaking radiation beams within the first region to the second layer of leaves. The processing device 140 may move the second layer of leaves to a position to shield the at least a portion of leaking radiation beams.

In some embodiments, the processing device 140 may cause a first portion of the second layer of leaves to shield the at least a portion of leaking radiation beams within the first region. Specifically, the processing device 140 may cause a second portion of the second layer of leaves to block a part of the second portion of the radiation beams. In some embodiments, the second portion of the second layer of leaves may also block at least a portion of radiation beams in a sub region within the first region. Further, the processing device 140 may cause the first portion of the second layer of leaves to shield the at least a portion of leaking radiation beams within a region of the first region other than the sub region.

Figure 9A:
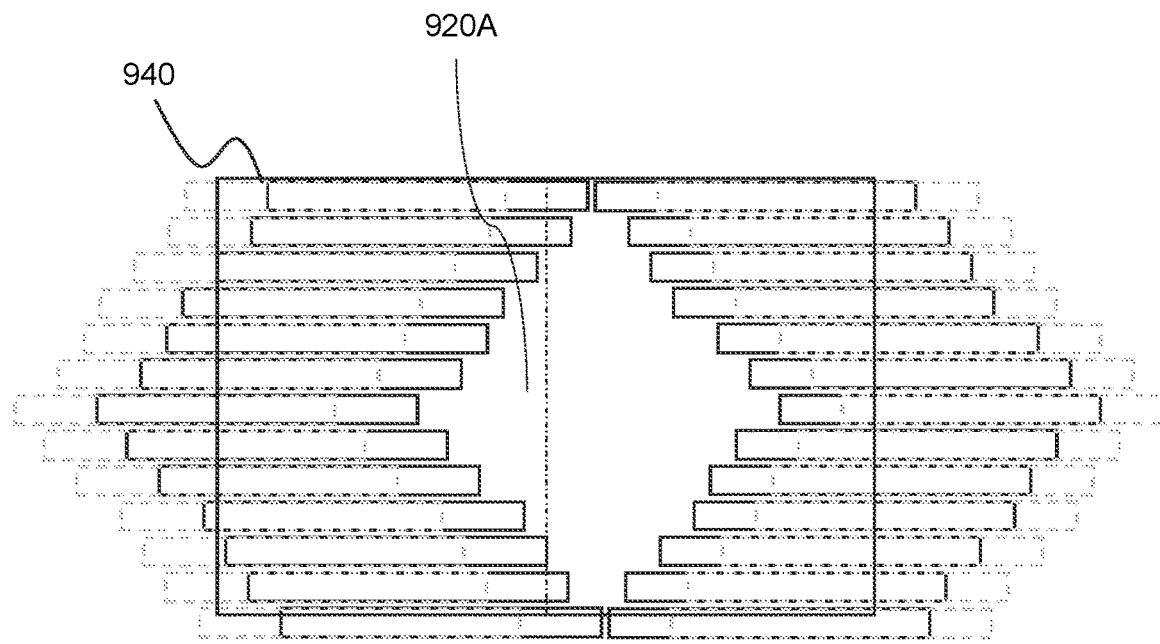
FIGS. 9A-9C are section views for operating a radiation treatment system according to some embodiments of the present disclosure.
Figure 9B:
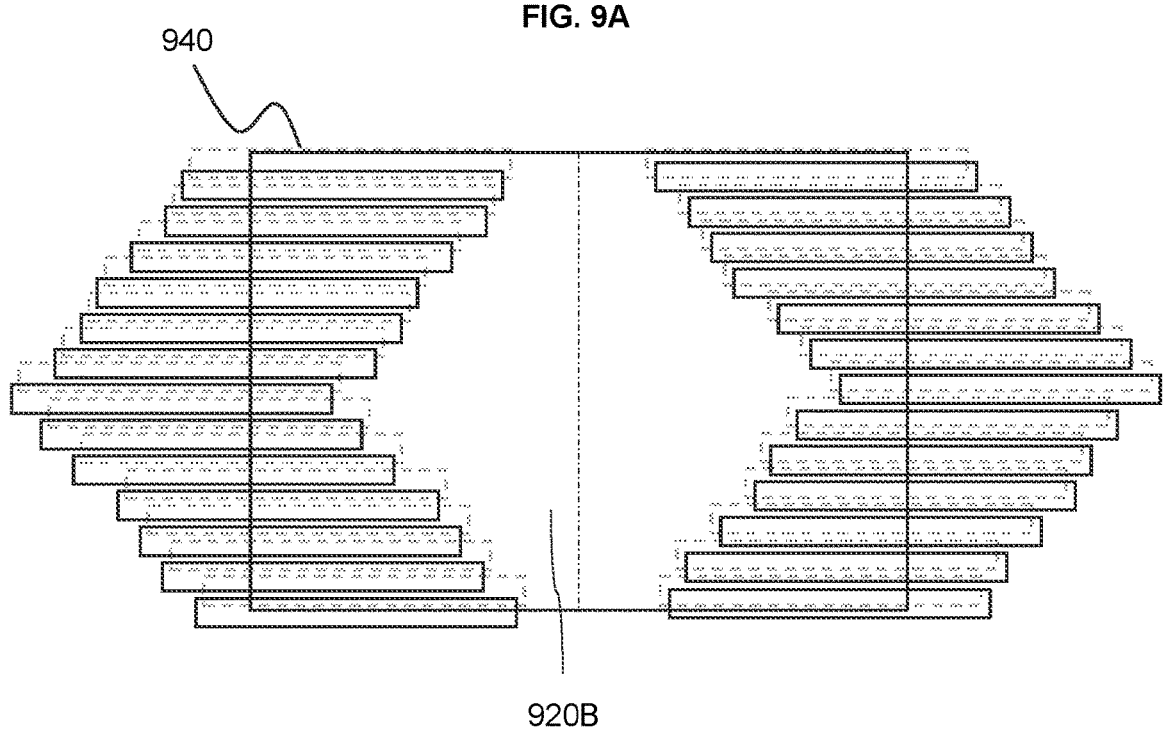
Figure 9C:
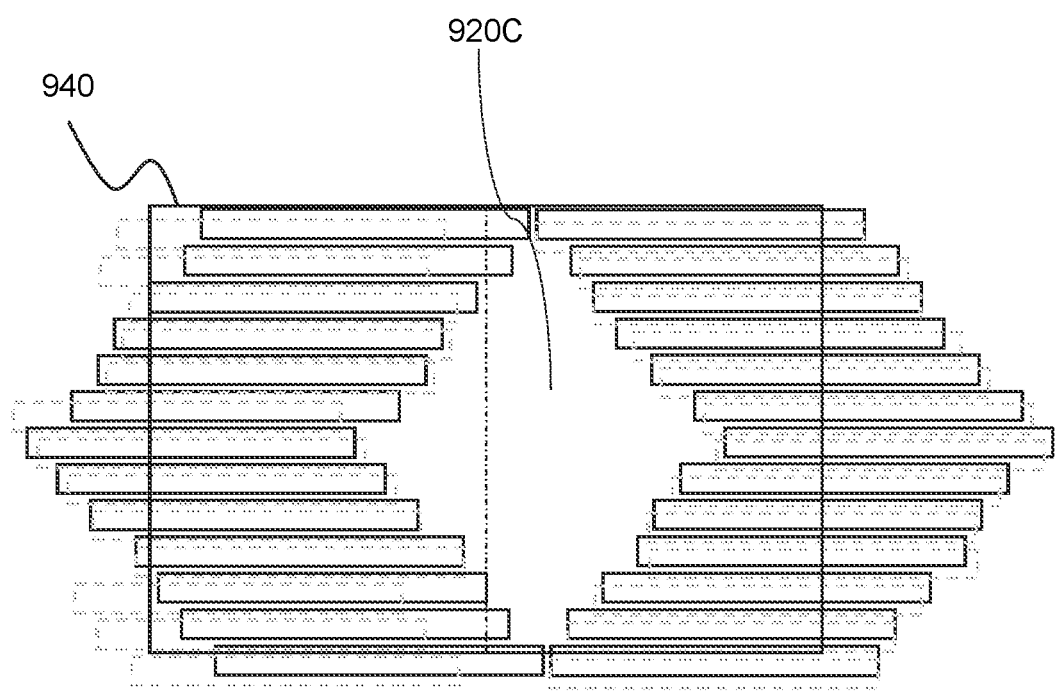

The second portion of the second layer of leaves may form the treatment region with the first layer of leaves. In some embodiments, the second portion of the second layer of leaves may move along with the first layer of leaves. A boundary of the treatment region may be formed based on a plurality of steps (e.g., as illustrated in FIG. 9C), and at least one width of the plurality of steps may be smaller than the width of each leaf. Thus the resolution (or the fine degree) of the boundary of the treatment region may be improved compared to a boundary of a treatment region formed by the first layer of leaves (e.g., as illustrated in FIG. 9A).

In response to a determination that the first region does not exist, the processing device 140 (e.g., the operation module 720) may cause the second layer of leaves to move to block a part of the second portion of radiation beams. In some embodiments, the processing device 140 may cause one or more leaves of the second layer of leaves to move to block the part of the second portion of the radiation beams. In some embodiments, the processing device 140 may cause all leaves of the second layer of leaves to move to block the part of the second portion of the radiation beams. In some embodiments, the processing device 140 may transmit an instruction for moving to block the part of the second portion of radiation beams to the second layer of leaves. A boundary of the treatment region may be formed based on a plurality of steps (e.g., as illustrated in FIG. 9B), and at least one width of the plurality of steps may be smaller than the width of each leaf. Thus the resolution (or the fine degree) of the boundary of the treatment region may be improved compared to a boundary of a treatment region formed by the first layer of leaves (e.g., as illustrated in FIG. 9A).

For illustration purposes, the MLC may at least include the first layer of leaves, and the second layer of leaves. In response to a determination that the first region exists, the processing device 140 may cause at least a portion of one or more layers of leaves other than the first layer of leaves and the second layer of leaves to move to block a part of the second portion of the radiation beams. In some embodiments, the at least a portion of the one or more layers of leaves other than the first layer of leaves and the second layer of leaves may also block at least a portion of radiation beams in a first sub region within the first region. Further, the processing device 140 may cause the second layer of leaves to shield the at least a portion of leaking radiation beams within a region of the first region other than the first sub region.

Similarly, in some embodiments, the processing device 140 may cause a first portion of the second layer of leaves to shield the at least a portion of leaking radiation beams within the first region. Specifically, the processing device 140 may cause a second portion of the second layer of leaves to block a part of the second portion of the radiation beams. In some embodiments, the second portion of the second layer of leaves may also block at least a portion of radiation beams in a second sub region within the first region. Further, the processing device 140 may cause the first portion of the second layer of leaves to shield the at least a portion of leaking radiation beams within a region of the first region other than the first sub region and the second sub region.

In response to a determination that the first region does not exist, the processing device 140 (e.g., the operation module 720) may cause at least a portion of the one or more layers of leaves and the second layer of leaves to move to block a part of the second portion of radiation beams. In some embodiments, the at least a portion of the one or more layer of leaves and the second layer of leaves may move along with the first layer of leaves. In some embodiments, the processing device 140 may transmit an instruction for moving to block a part of the second portion of radiation beams to the layer of leaves other than the first layer of leaves.

By providing the method described above, the MLC may simultaneously form the treatment region and block at least a portion of the leaking radiation beams delivered to the normal portion of the object other than the lesion. In some cases, a boundary of the treatment region may be formed based on a plurality of steps, and at least one width of the plurality of steps may be smaller than the width of each leaf. Thus the resolution (or the fine degree) of the boundary of the treatment region may be improved compared to a boundary of a treatment region formed by the first layer of leaves.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIGS. 9A-9C are section views for operating a radiation treatment system according to some embodiments of the present disclosure. The radiation treatment system may be an example of the radiation treatment system as illustrated in FIG. 8. It should be noted that FIGS. 9A-9C only illustrate a portion of components of the radiation treatment system. The portion of components of the radiation treatment system may be configured to form an aperture through which a portion of radiation beams is delivered to a treatment region. The radiation treatment system may also include an imaging assembly (e.g., CT, CBCT), a treatment radiation source (e.g., the first radiation source 114), a gantry (e.g., the gantry 111), a table (e.g., the table 115), etc.

The radiation treatment system may include an MLC. The MLC may have a first layer of leaves and a second layer of leaves. As illustrated in FIGS. 9A-9C, rectangles with solid lines may represent leaves in the first layer of leaves. Rectangles with dotted lines may represent leaves in the second layer of leaves. A rectangle 940 may represent a radiation area of the first radiation source 114. As illustrated in FIG. 9A, the first layer of leaves may fail to block leaking radiation beams within a first region, and the second layer of leaves may be moved to shield at least a portion of the leaking radiation beams within the first region. As illustrated in FIG. 9B, the first layer of leaves may block leaking radiation beams within the first region, the second layer of leaves may move along with the first layer of leaves. As illustrated in FIG. 9C, the first layer of leaves may fail to block leaking radiation beams within a first region. A portion of the second layer of leaves may be moved to shield at least a portion of the leaking radiation beams within the first region. A second portion of the second layer of leaves may form the treatment region with the first layer of leaves.

As illustrated in FIG. 9A, a boundary of the treatment region 920A may be formed based on a plurality of steps, and a width of each step may be the same as a width of each leaf of the first layer of leaves. As illustrated in FIG. 9B, a boundary of the treatment region 920B may be formed based on a plurality of steps, and a width of each step may be smaller than or equal to the width of each leaf of the first layer of leaves or the second layer of leaves. As illustrated in FIG. 9C, a boundary of the treatment region 920C may be formed based on a plurality of steps, and a width of each step may be smaller than or equal to the width of each leaf of the first layer of leaves or the second layer of leaves. As described in FIG. 1, the resolution may be used to represent a fine degree of a boundary of a treatment region (or aperture). The higher the resolution is, the finer the boundary of the treatment region may be. A resolution of a boundary of the treatment region 920B may be higher than a resolution of a boundary of the treatment region 920A. A resolution of the boundary of the treatment region 920C may be higher than a resolution of the boundary of the treatment region 920A.

In some embodiments, the present disclosure may provide a radiation treatment system at least including an MLC having at least two layers of leaves and at least one block. In some embodiments, the at least two layers of leaves may be arranged stacked one above another. In some embodiments, the at least two layers of leaves may be arranged in parallel and have an offset such that each leaf in first layer of leaves may be offset from a leaf in second layer of leaves, e.g., in the longitudinal direction. At least a portion of the leaves may be movable to block pathways of a first portion of radiation beams within a radiation area. A second portion of the radiation beams the MLC may be incident at a treatment region of the radiation treatment system 100. As described above, the treatment region should conform to the shape of the lesion. The lesion (e.g., the tumor) of the object may be located at the treatment region for radiotherapy. Thus the first portion and/or the second portion of radiation beams may relate to the shape of the lesion. For illustration purposes, the first portion of radiation beams may include at least a portion of radiation beams other than a portion (e.g., the second portion) of radiation beams within the treatment region. Each of the at least two layers of leaves may be similar to or the same as the layer of leaves described in FIG. 1.

The MLC may be situated in a first plane. The at least one block may be situated in a second plane different from the first plane. The at least one block may be configured to block at least a portion of leaking radiation beams within a first region other than the treatment region. As used herein, a first layer of leaves of the MLC may fail to block leaking radiation beams within the first region. In some embodiments, the at least one block may be made of radiation impermeable materials (e.g., tungsten, lead, steel alloy, tungsten alloy). The at least one block may be arranged along a direction of the radiation beams towards the object. Projection of the at least one block may at least cover the first region thereby blocking the at least a portion of leaking radiation beams within the first region. The at least one block may be similar to or the same as the at least one block described in FIG. 5A-5B. More detailed descriptions of the at least one block can be found elsewhere in the present disclosure. See, e.g., FIGS. 5A-5B and the descriptions thereof.

Figure 10:
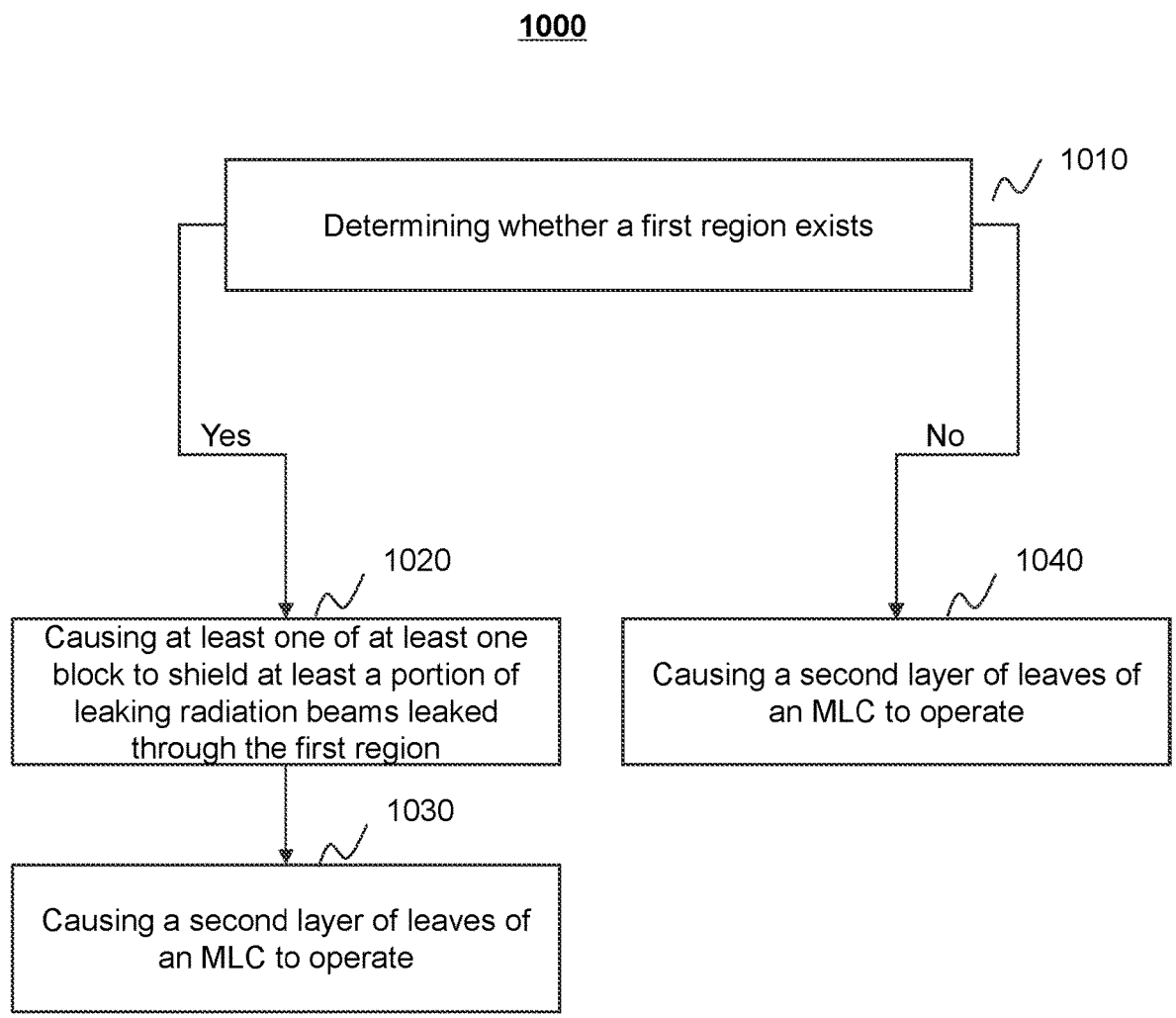
FIG. 10 is a flowchart illustrating an exemplary process for operating a radiation treatment system according to some embodiments of the present disclosure.

FIG. 10 is a flowchart illustrating an exemplary process 1000 for operating the radiation treatment system according to some embodiments of the present disclosure. The process 1000 may be implemented in the radiation treatment system 100 illustrated in FIG. 1. For example, the process 1000 may be stored in the storage device 150 and/or the storage 220 in the form of instructions (e.g., an application), and invoked and/or executed by the processing device 140 (e.g., the processor 210 illustrated in FIG. 2, the CPU 340 as illustrated in FIG. 3, or one or more modules in the processing device 140 illustrated in FIG. 7). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1010, the processing device 140 (e.g., the determination module 710) may determine whether the first region exists. As described above, the first region may form when one or more leaves of the first group of the first layer of leaves pass across a first line such that the first region is exposed to allow at least a portion of the first portion of the radiation beams to leak through. More detailed descriptions of the first line can be found elsewhere in the present disclosure. See, e.g., FIGS. 4A-6B.

In response to a determination that the first region exists, the processing device 140 (e.g., the operation module 720) may cause at least one of the at least one block or a second layer of leaves of the MLC to operate. In some embodiments, if the at least one block is fixed, projection of the at least one block in the first plane may cover the first region thereby blocking the at least a portion of leaking radiation beams within the first region. The processing device 140 may operate one or more layers of leaves other than the first layer of leaves of the MLC to operate in 1030. In some embodiments, the processing device 140 may operate at least a portion of the layer of leaves other than the first layer of leaves to block a part of the second portion of the radiation beams. In some embodiments, the at least a portion of the one or more layers of leaves other than the first layer of leaves may move along with the first layer of leaves.

In some embodiments, if the at least one block is moveable, the processing device 140 may first determine whether the at least one block is able to move. In response to a determination that the at least one block is able to move, the processing device 140 may cause the at least one block to move to shield the at least a portion of radiation beams leaked through the first region in 1020. The processing device 140 may operate the one or more layers of leaves other than the first layer of leaves of the MLC to operate in 1030. In some embodiments, the processing device 140 may operate at least a portion of the one or more layers of leaves other than the first layer of leaves to block a part of the second portion of the radiation beams. In some embodiments, the at least a portion of the one or more layers of leaves other than the first layer of leaves may move along with the first layer of leaves. In response to a determination that the at least one block is unable to move, the processing device 140 may operate the MLC similar to the process 800, and not repeated here.

In response to a determination that the first region does not exist, the processing device 140 may cause the one or more layers of leaves other than the first layer of leaves to move to form the treatment region. In some embodiments, the processing device 140 may operate at least a portion of the one or more layers of leaves other than the first layer of leaves to block a part of the second portion of the radiation beams. In some embodiments, the at least a portion of the one or more layers of leaves other than the first layer of leaves may move along with the first layer of leaves.

By providing the method described above, when the at least one block fails to block the at least a portion of leaking radiation beams, the MLC may be operated to block the at least a portion of leaking radiation beams, thereby ensuring the leaking radiation beams not to be delivered to the normal portion of the object other than the lesion. In some cases, a boundary of the treatment region may be formed based on a plurality of steps. At least one width of the plurality of steps may be smaller than the width of each leaf. Thus the resolution (or the fine degree) of the boundary of the treatment region may be improved compared to a boundary of a treatment region formed by the first layer of leaves.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 11A:
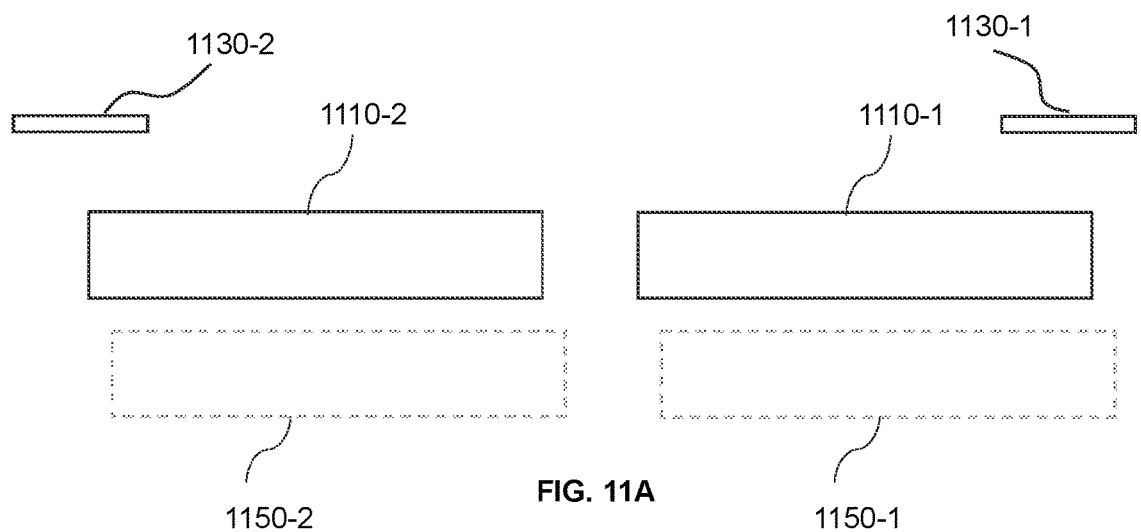
FIGS. 11A-11B are section views for operating a radiation treatment system according to some embodiments of the present disclosure.
Figure 11B:
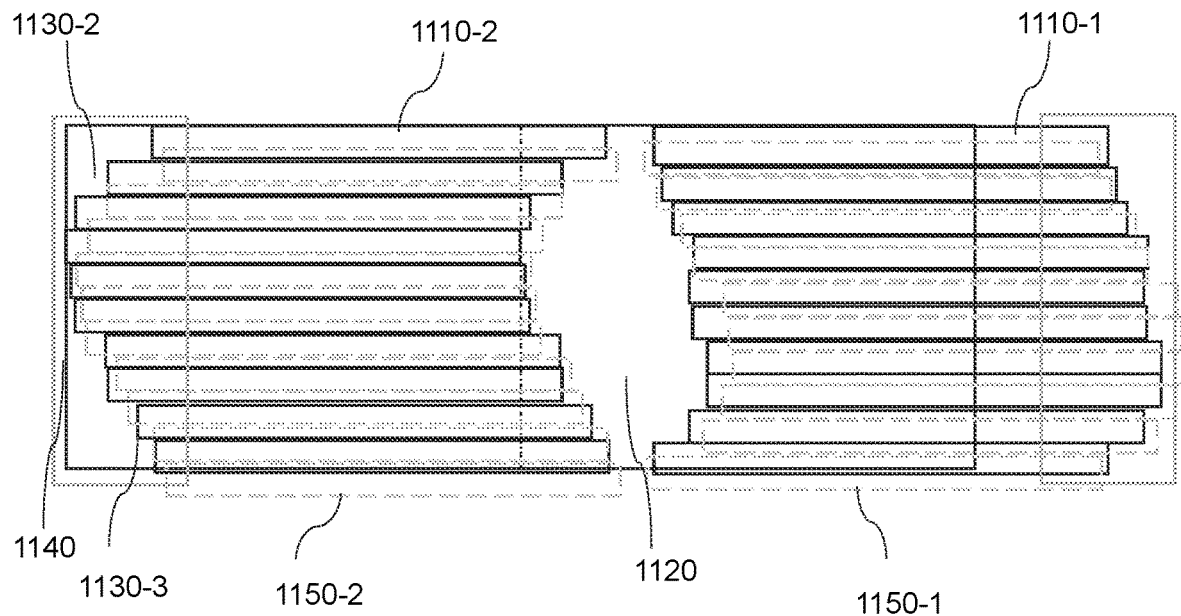

FIGS. 11A and 11B are section views for operating a radiation treatment system 1100 according to some embodiments of the present disclosure. The radiation treatment system 1100 may be an example of the radiation treatment system described in FIG. 10. It should be noted that FIGS. 11A-11B only illustrate a portion of components of the radiation treatment system 1100. The portion of components of the radiation treatment system 1100 may be configured to form an aperture through which a portion of radiation beams is delivered to a treatment region. The radiation treatment system 1100 may also include an imaging assembly (e.g., CT, CBCT), a treatment radiation source (e.g., the first radiation source 114), a gantry (e.g., the gantry 111), a table (e.g., the table 115), etc.

The radiation treatment system 1100 may include an MLC having two layers of leaves, a first block 1130-1, and a second block 1130-2. A first layer of leaves of the MLC may include a first group of leaves 1110-1 (also referred to as "leaves 1110-1") and a second group of leaves 1110-2 (also referred to as leaves 1110-2"). A second layer of leaves of the MLC may include a first group of leaves 1150-1 (also referred to as "leaves 1150-1") and a second group of leaves 1150-2 (also referred to as leaves 1150-2"). The first block 1130-1 may be situated above the leaves 1110-1. The second block 1130-2 may be situated above the leaves 1110-2.

As illustrated in FIG. 11B, a rectangle 1140 may represent a radiation area (the maximum of the radiation area of the first radiation source 114). The two layers of leaves may move along with each other to form an aperture through which a portion of radiation beams is delivered to a treatment region. A region formed by front ends of the leaves 1110-1, the leaves 1110-2, the leaves 1150-1, and the leaves 1150-2 may constitute the treatment region, e.g., a region 1120 as illustrated in FIG. 11B. Projection of the two blocks in a plane of the MLC may cover a region 1130-1, and a region 1130-2, thereby blocking leaking radiation beams within a first region constituted by the region 1130-1, and the region 1130-2.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

Some embodiments of the present invention can also be embodied as follows:

Embodiment 1: A radiation treatment system, comprising:
a multi-leaf collimator (MLC), wherein the MLC includes at least one layer of leaves, each of the at least one layer of leaves includes a first group of leaves and a second group of leaves, the first group of leaves and the second group of leaves are configured to shield at least a portion of radiation beams within a radiation area by blocking pathways of the at least a portion of radiation beams, an end area forms in the radiation area when at least one leaf of the first group of leaves or of the second group of leaves moves so that the MLC fails to block pathways of leaking radiation beams in the end area; and at least one block situated above the MLC, wherein the at least one block is configured to shield at least a portion of the leaking radiation beams within the end area.

Embodiment 2: The radiation treatment system of embodiment 1, wherein:
an area of the end area changes when at least one leaf of the first group of leaves or at least one leaf of the second group of leaves moves.

Embodiment 3: The radiation treatment system of embodiment 1 or 2, wherein:
the end area includes a first section that forms when one or more leaves of the first group of leaves pass across a first line.

Embodiment 4: The radiation treatment system of embodiment 3, wherein:
the first line is a centerline of the radiation area, and
a length of at least one of the first group of leaves is equal to or shorter than a half of a width of the radiation area.

Embodiment 5: The radiation treatment system of any one of embodiments 1-4, wherein:
the end area includes a second section that forms when one or more leaves of the second group of leaves pass across a second line.

Embodiment 6: The radiation treatment system of embodiment 5, wherein:
the second line is a centerline of the radiation area, and
a length of at least one of the second group of leaves is equal to or shorter than a half of a width of the radiation area.

Embodiment 7: The radiation treatment system of any one of embodiments 1-6, wherein:
each of the first group of leaves has a same length.

Embodiment 8: The radiation treatment system of any one of embodiments 1-7, wherein:
each of the second group of leaves has a same length.

Embodiment 9: The radiation treatment system of any one of embodiments 1-8, wherein the at least one block includes a first block situated above the first group of leaves and a second block situated above the second group of leaves.

Embodiment 10: The radiation treatment system of any one of embodiments 1-9, wherein a length of each of the at least one block relates to at least one of: a first reference distance that at least one leaf of the first group of leaves is allowed to move, a second reference distance that at least one leaf of the second group of leaves is allowed to move, a size of each of the at least one layer of leaves, a length of at least one leaf of the first group of leaves, or a length of at least one leaf of the second group of leaves.

Embodiment 11: The radiation treatment system of any one of embodiments 1-10, wherein at least one of the at least one block is movable along with the first group of leaves or the second group of leaves.

Embodiment 12: The radiation treatment system of any one of embodiments 1-10, wherein at least one of the at least one block is fixed.

Embodiment 13: The radiation treatment system of any one of embodiments 1-12, wherein the at least one layer of leaves includes more than one layer of leaves.

Embodiment 14: The radiation treatment system of any one of embodiments 1-13, wherein at least a portion of the radiation treatment system is configured to form a treatment region.

Embodiment 15: The radiation treatment system of any one of embodiments 1-14, further comprising: a radiation delivery device that delivers the radiation beams in the radiation area.

Embodiment 16: A method for operating a radiation treatment system, the method being implemented on a computing device having at least one processor, and at least one computer-readable storage medium, wherein:

the radiation treatment system includes a multi-leaf collimator (MLC) having at least two layers of leaves and configured to shield at least a portion of radiation beams in a radiation area by blocking pathways of the at least a portion of radiation beams, an end area forms in the radiation area when a first layer of leaves of the MLC moves so as to fail to block pathways of leaking radiation beams, and the method includes:

determining whether the first layer of leaves of the MLC fail to shield the end area; and causing, based on a determination result, a second layer of leaves of the MLC to operate.

Embodiment 17: The method of embodiment 16, wherein the determination result includes that the first layer of leaves fail to shield the end area, and the causing a second layer of leaves of the MLC to operate includes:

causing the second layer of leaves to move independently of the first layer of leaves such that the second layer of leaves shields at least a portion of the leaking radiation beams within the end area.

Embodiment 18: The method of embodiment 16, wherein the determination result includes that the first layer of leaves shields the end area, and the causing a second layer of leaves of the MLC to operate includes:

causing the second layer of leaves to move along with the first layer of leaves.

Embodiment 19: The method of any one of embodiments 16-18, wherein:

the first layer of leaves includes a first group of leaves and a second group of leaves, and an area of the end area changes when at least one leaf of the first group of leaves or at least one leaf of the second group of second leaves moves.

Embodiment 20: The method of embodiment 19, wherein:

the end area includes a first section that forms when one or more leaves of the first group of leaves pass across a first line.

Embodiment 21: The method of embodiment 20, wherein:

the first line is a centerline of the radiation area, and a length of at least one leave of the first group of leaves is equal to or shorter than a half of a width of the radiation area.

Embodiment 22: The method of embodiment 19, wherein:

the end area includes a second section that forms when one or more leaves of the second group of leaves pass across a second line.

Embodiment 23: The method of embodiment 22, wherein:

the second line is a centerline of the radiation area, and a length of at least one leave of the second group of leaves is equal to or shorter than a half of a width of the radiation area.

Embodiment 24: The method of any one of embodiments 16-23, wherein the at least two layers of leaves include two layer of leaves.

Embodiment 25: The method of any one of embodiments 16-24, wherein the MLC includes more than two layers of leaves, and the method include:

causing at least one layer of leaves of the MLC other than the second layer of leaves to move along with the first layer of leaves.

Embodiment 26: The method of any one of embodiments 16-25, wherein the radiation treatment system further includes at least one block situated above the MLC, and the method further comprises:

using the at least one block to shield at least a portion of the leaking radiation beams within the end area.

Embodiment 27: A system, comprising:

at least one storage device including a set of instructions for operating a radiation treatment system, wherein:

the radiation treatment system includes a multi-leaf collimator (MLC) having at least two layers of leaves and configured to shield at least a portion of radiation beams in a radiation area by blocking pathways of the at least a portion of radiation beams, and an end area forms in the radiation area when a first layer of leaves of the MLC moves so as to fail to block pathways of leaking radiation beams; and at least one processor in communication with the at least one storage device, wherein when executing the set of instructions, the at least one processor is configured to cause the system to perform operations including:

determining whether the first layer of leaves of the MLC fail to shield the end area; and causing, based on a determination result, a second layer of leaves of the MLC to operate.

Embodiment 28: The system of embodiment 27, wherein the determination result includes that the first layer of leaves fail to shield the end area, and to cause a second layer of leaves of the MLC to operate, the at least one processor is configured to cause the system to perform operations including:

causing the second layer of leaves to move independently of the first layer of leaves such that the second layer of leaves shields at least a portion of the leaking radiation beams within the end area.

Embodiment 29: The system of embodiment 27, wherein the determination result includes that the first layer of leaves shields the end area, and to cause a second layer of leaves of the MLC to operate, the at least one processor is configured to cause the system to perform operations including:

causing the second layer of leaves to move along with the first layer of leaves.

Embodiment 30: The system of any one of embodiments 27-29, wherein:

the first layer of leaves includes a first group of leaves and a second group of leaves, and an area of the end area changes when at least one leaf of the first group of leaves or at least one leaf of the second group of second leaves moves.

Embodiment 31: The system of embodiment 30, wherein:

the end area includes a first section that forms when one or more leaves of the first group of leaves pass across a first line.

Embodiment 32: The system of embodiment 31, wherein:

the first line is a centerline of the radiation area, and a length of at least one leave of the first group of leaves is equal to or shorter than a half of a width of the radiation area.

Embodiment 33: The system of embodiment 30, wherein:
the end area includes a second section that forms when one or more leaves of the second group of leaves pass across a second line.

Embodiment 34: The system of embodiment 33, wherein:
the second line is a centerline of the radiation area, and
a length of at least one leave of the second group of leaves is equal to or shorter than a half of a width of the radiation area.

Embodiment 35: The system of any one of embodiments 27-34, wherein the at least two layers of leaves include two layers of leaves.

Embodiment 36: The system of any one of embodiments 27-35, wherein the MLC includes more than two layers of leaves, and the at least one processor is configured to cause the system to perform operations including:
causing at least one layer of leaves of the MLC other than the second layer of leaves to move along with the first layer of leaves.

Embodiment 37: The system of any one of embodiments 28-36, wherein the radiation treatment system further includes at least one block situated above the MLC, and the at least one processor is configured to cause the system to perform operations including:
using the at least one block to shield at least a portion of the leaking radiation beams within the end area.

Embodiment 38: A method for operating a radiation treatment system, the method being implemented on a computing device having at least one processor, and at least one computer-readable storage medium, wherein:
the radiation treatment system includes a multi-leaf collimator (MLC) having at least two layers of leaves and at least one block situated above the MLC, the MLC being configured to shield at least a portion of radiation beams in a radiation area by blocking pathways of the at least a portion of radiation beams,
an end area forms in the radiation area when a first layer of leaves of the MLC moves so as to fail to block pathways of leaking radiation beams, and the method includes:
determining whether the first layer of leaves of the MLC fail to shield the end area; and
causing, based on a determination result, a second layer of leaves of the MLC and the at least one block to operate.

Embodiment 39: The method of embodiment 38, wherein the determination result includes that the first layer of leaves fail to shield the end area, and the causing a second layer of leaves of the MLC and the at least one block to operate includes:
causing the at least one block to shield at least a portion of the leaking radiation beams within the end area; and
causing the second layer of leaves to move along with the first layer of leaves.

Embodiment 40: The method of embodiment 38, wherein the determination result includes that the first layer of leaves shields the end area, and the causing a second layer of leaves of the MLC to operate includes:
causing the second layer of leaves to move along with the first layer of leaves.

Embodiment 41: The method of any one of embodiments 38-40, wherein:
the first layer of leaves includes a first group of leaves and a second group of leaves, and
an area of the end area changes when at least one leaf of the first group of leaves or at least one leaf of the second group of second leaves moves.

Embodiment 42: The method of embodiment 41, wherein:
the end area includes a first section that forms when one or more leaves of the first group of leaves pass across a first line.

Embodiment 43: The method of embodiment 42, wherein:
the first line is a centerline of the radiation area, and
a length of at least one leave of the first group of leaves is equal to or shorter than a half of a width of the radiation area.

Embodiment 44: The method of embodiment 41, wherein:
the end area includes a second section that forms when one or more leaves of the second group of leaves pass across a second line.

Embodiment 45: The method of embodiment 44, wherein:
the second line is a centerline of the radiation area, and
a length of at least one leave of the second group of leaves is equal to or shorter than a half of a width of the radiation area.

Embodiment 46: The method of any one of embodiments 41-45, wherein a length of each of the at least one block relates to at least one of: a first reference distance that at least one leaf of the first group of leaves is allowed to move, a second reference distance that at least one leaf of the second group of leaves is allowed to move, a size of each of the at least one layer of leaves, a length of at least one leaf of the first group of leaves, or a length of at least one leaf of the second group of leaves.

Embodiment 47: The method of any one of embodiments 38-46, wherein at least one of the at least one block is movable along with the first group of leaves or the second group of leaves.

Embodiment 48: The method of any one of embodiments 38-47, wherein at least one of the at least one block is fixed.

Embodiment 49: The method of any one of embodiments 38-48, wherein the at least two layers of leaves include two layers of leaves.

Embodiment 50: A system, comprising:
at least one storage device including a set of instructions for operating a radiation treatment system, wherein:
the radiation treatment system includes a multi-leaf collimator (MLC) having at least two layers of leaves and at least one block situated above the MLC, the MLC being configured to shield at least a portion of radiation beams in a radiation area by blocking pathways of the at least a portion of radiation beams,
an end area forms in the radiation area when a first layer of leaves of the MLC moves so as to fail to block pathways of leaking radiation beams, and the at least one processor is configured to cause the system to perform operations including:
determining whether the first layer of leaves of the MLC fail to shield the end area; and
causing, based on a determination result, a second layer of leaves of the MLC and the at least one block to operate.

Embodiment 51: The system of embodiment 50, wherein the determination result includes that the first layer of leaves fail to shield the end area, and to cause a second layer of leaves of the MLC and the at least one block to operate, the at least one processor is configured to cause the system to perform operations including:
causing the at least one block to shield at least a portion of the leaking radiation beams within the end area; and
causing the second layer of leaves to move along with the first layer of leaves.

Embodiment 52. The system of embodiment 50, wherein the determination result includes that the first layer of leaves shields the end area, and to cause a second layer of leaves of the MLC to operate, the at least one processor is configured to cause the system to perform operations including:
    causing the second layer of leaves to move along with the first layer of leaves.

Embodiment 53: The system of any one of embodiments 50-52, wherein:
    the first layer of leaves includes a first group of leaves and a second group of leaves, and
    an area of the end area changes when at least one leaf of the first group of leaves or at least one leaf of the second group of second leaves moves.

Embodiment 54: The system of embodiment 53, wherein:
    the end area includes a first section that forms when one or more leaves of the first group of leaves pass across a first line.

Embodiment 55: The system of embodiment 54, wherein:
    the first line is a centerline of the radiation area, and
    a length of at least one leave of the first group of leaves is equal to or shorter than a half of a width of the radiation area.

Embodiment 56: The system of embodiment 53, wherein:
    the end area includes a second section that forms when one or more leaves of the second group of leaves pass across a second line.

Embodiment 57: The system of embodiment 56, wherein:
    the second line is a centerline of the radiation area, and
    a length of at least one leave of the second group of leaves is equal to or shorter than a half of a width of the radiation area.

Embodiment 58: The system of any one of embodiments 53-57, wherein a width of each of the at least one block relates to at least one of: a first reference distance that at least one leaf of the first group of leaves is allowed to move, a second reference distance that at least one leaf of the second group of leaves is allowed to move, a size of each of the at least one layer of leaves, a length of at least one leaf of the first group of leaves, or a length of at least one leaf of the second group of leaves.

Embodiment 59: The system of any one of embodiments 50-58, wherein at least one of the at least one block is movable along with the first group of leaves or the second group of leaves.

Embodiment 60: The system of any one of embodiments 50-59, wherein at least one of the at least one block is fixed.

Embodiment 61: The system of any one of embodiments 50-60, wherein the at least two layers of leaves include two layers of leaves.

Embodiment 62: A non-transitory computer readable medium, comprising:
    instructions being executed by at least one processor, causing the at least one processor to implement a method, wherein:
    the radiation treatment system includes an MLC having at least two layers of leaves and configured to shield at least a portion of radiation beams in a radiation area by blocking pathways of the at least a portion of radiation beams,
    an end area forms in the radiation area when a first layer of leaves of the MLC moves so as to fail to block pathways of leaking radiation beams, and the method includes:
        determining whether the first layer of leaves of the MLC fail to shield the end area; and
        causing, based on a determination result, a second layer of leaves of the MLC to operate.

Embodiment 63: A non-transitory computer readable medium, comprising:
    instructions being executed by at least one processor, causing the at least one processor to implement a method, wherein:
    the radiation treatment system includes a multi-leaf collimator (MLC) having at least two layers of leaves and configured to shield at least a portion of radiation beams in a radiation area by blocking pathways of the at least a portion of radiation beams, and
    an end area forms in the radiation area when a first layer of leaves of the MLC moves so as to fail to block pathways of leaking radiation beams; and
    at least one processor in communication with the at least one storage device, wherein when executing the set of instructions, the at least one processor is configured to cause the system to perform operations including:
        determining whether the first layer of leaves of the MLC fail to shield the end area; and
        causing, based on a determination result, a second layer of leaves of the MLC to operate.

Embodiment 64: A radiation treatment system, comprising:
    a radiation source configured to emit radiation beams; and
    a multi-leaf collimator (MLC) situated in a first plane, wherein the MLC includes at least one layer of leaves, each of the at least one layer of leaves includes a first group of leaves and a second group of leaves, at least a portion of the leaves being movable to block pathways of a first portion of the radiation beams within a radiation area, wherein a second portion of the radiation beams passing through the MLC is incident at a treatment region of the radiation treatment system, an isocenter of the radiation treatment system is within the treatment region; and
    at least one block situated in a second plane different from the first plane, wherein the at least one block is configured to shield at least a portion of leaking radiation beams within an end area, wherein the end area forms when the MLC fails to block pathways of the leaking radiation beams within the end area.

Embodiment 65: The radiation treatment system of embodiment 64, wherein the MLC and the at least one block are arranged along a direction of the radiation beams towards an object.

Embodiment 66: The radiation treatment system of embodiment 64 or 65, wherein:
    the end area includes a first section that forms when one or more leaves of the first group of at least one of the at least one layer of leaves pass across a first line such that the first section is exposed to allow at least a portion of the first portion of the radiation beams to leak through.

Embodiment 67: The radiation treatment system of embodiment 66, wherein:
    the first line is a centerline of the radiation area, and
    a length of at least one of the first group of leaves is equal to a half of a length of the radiation area.

Embodiment 68: The radiation treatment system of embodiment 66 or 67, wherein:
    the end area includes a second section that forms when one or more leaves of the second group of at least one of the at least one layer of leaves pass across a second line such that the second section is exposed to allow at least a portion of the first portion of the radiation beams to leak through.

Embodiment 69: The radiation treatment system of embodiment 68, wherein:
    the second line is a centerline of the radiation area, and
    a length of at least one of the second group of leaves is equal to a half of a length of the radiation area.

Embodiment 70: The radiation treatment system of any one of embodiments 64-69, wherein the at least one block includes a first block and a second block situated in the second plane.

Embodiment 71: The radiation treatment system of any one of embodiments 64-70, wherein at least one of the at least one block, or a portion thereof, is movable.

Embodiment 72. The radiation treatment system of any one of embodiments 64-71, wherein at least one of the at least one block is fixed, and projection of the at least one of the at least one block on the first plane at least partially overlaps the MLC.

Embodiment 73: The radiation treatment system of any one of embodiments 64-72, wherein a size of each of the at least one block relates to at least one of: a first reference distance that at least one leaf of the first group of leaves is allowed to move, a second reference distance that at least one leaf of the second group of leaves is allowed to move, a size of each of the at least one layer of leaves, a length of at least one leaf of the first group of leaves, or a length of at least one leaf of the second group of leaves.

Embodiment 74: A method for operating a multi-leaf collimator (MLC), the method being implemented on a computing device having at least one processor, and at least one computer-readable storage medium, wherein:

the MLC includes at least a first layer of leaves and a second layer of leaves, each of the first layer of leaves and the second layer of leaves includes a first group of leaves and a second group of leaves, at least a portion of the leaves being movable to block pathways of a first portion of the radiation beams within a radiation area, wherein a second portion of the radiation beams passing through the MLC is incident at a treatment region of the radiation treatment system, an isocenter of the radiation treatment system is within the treatment region, and the method includes:

determining whether a first region exists, wherein the first region forms when one or more leaves of the first group of the first layer of leaves pass across a first line such that the first region is exposed to allow at least a portion of the first portion of the radiation beams to leak through; and causing, based on a determination result, the second layer of leaves of the MLC to operate.

Embodiment 75: The method of embodiment 74, wherein:

the first line is a centerline of the radiation area, and a length of at least one of the first group of leaves is equal to a half of a length of the radiation area.

Embodiment 76: The method of embodiment 74 or 75, wherein the determination result includes that the first region exists, and the causing the second layer of leaves of the MLC to operate includes:

causing the second layer of leaves to move to shield at least a portion of radiation beams leaked through the first region.

Embodiment 77: The method of embodiment 74 or 75, wherein the determination result includes that the first region does not exist, and the causing the second layer of leaves of the MLC to operate includes:

causing one or more leaves of the second layer of leaves to move to block a part of the second portion of the radiation beams.

Embodiment 78: A method for operating a radiation treatment system, the method being implemented on a computing device having at least one processor, and at least one computer-readable storage medium, wherein:

the radiation treatment system includes a multi-leaf collimator (MLC) and at least one block, the MLC includes at least one layer of leaves, each of the at least one layer of leaves includes a first group of leaves and a second group of leaves, at least a portion of the leaves being movable to block pathways of a first portion of the radiation beams within a radiation area, wherein a second portion of the radiation beams passing through the MLC is incident at a treatment region of the radiation treatment system, an isocenter of the radiation treatment system is within the treatment region, and the method includes:

determining whether a first region exists, wherein the first region forms when one or more leaves of the first group of the first layer of leaves pass across a first line such that the first region is exposed to allow at least a portion of the first portion of the radiation beams to leak through; and causing, based on a determination result, at least one of the at least one block or the second layer of leaves of the MLC to operate.

Embodiment 79: The method of embodiment 78, wherein the at least one block is fixed in the second plane, and projection of the at least one of the at least one block at least partially overlaps the MLC.

Embodiment 80: The method of embodiment 78, wherein the determination result includes that the first region exists, and the causing at least one of the at least one block or the second layer of leaves of the MLC to operate includes:

causing one or more leaves of the second layer of leaves to move to block a part of the second portion of the radiation beams.

Embodiment 81: The method of embodiment 78, wherein the at least one block is moveable, the determination result includes that the first region exists, and the causing at least one of the at least one block or the second layer of leaves of the MLC to operate includes:

determining whether the at least one block is able to move; and causing, based on a second determination result, the second layer of leaves to operate.

Embodiment 82: The method of embodiment 81, wherein the causing, based on a second determination result, the second layer of leaves to operate includes:

in response to the second determination that the at least one block is able to move, causing the at least one block to shield at least a portion of the radiation beams that leak through the first region, and causing the second layer of leaves to move to block a part of the second portion of the radiation beams; or in response to the second determination that the at least one block is unable to move, causing the second layer of leaves to shield at least a portion of the radiation beams that leak through the first region.

Embodiment 83: The method of embodiment 78, wherein the determination result includes that the first region does not exist, and the causing at least one of the at least one block or the second layer of leaves of the MLC to operate includes:

causing one or more leaves of the second layer of leaves to move to block a part of the second portion of the radiation beams.

Embodiment 84: A non-transitory computer readable medium, comprising:

instructions being executed by at least one processor, causing the at least one processor to implement a method, wherein:

a multi-leaf collimator (MLC) includes at least a first layer of leaves and a second layer of leaves, each of the first layer of leaves and the second layer of leaves includes a first group of leaves and a second group of leaves, at least a portion of the leaves being movable to block pathways of a first portion of the radiation beams within a radiation area, wherein a second portion of the radiation beams passing through the MLC is incident at a treatment region of the radiation treatment system, an isocenter of the radiation treatment system is within the treatment region, and
  the method includes:
    determining whether a first region exists, wherein the first region forms when one or more leaves of the first group of the first layer of leaves pass across a first line such that the first region is exposed to allow at least a portion of the first portion of the radiation beams to leak through; and
    causing, based on a determination result, the second layer of leaves of the MLC to operate.

Embodiment 85: A non-transitory computer readable medium, comprising:
  instructions being executed by at least one processor, causing the at least one processor to implement a method, wherein:
    a radiation treatment system includes
    a multi-leaf collimator (MLC) and at least one block, the MLC includes at least one layer of leaves, each of the at least one layer of leaves includes a first group of leaves and a second group of leaves, at least a portion of the leaves being movable to block pathways of a first portion of the radiation beams within a radiation area, wherein a second portion of the radiation beams passing through the MLC is incident at a treatment region of the radiation treatment system, an isocenter of the radiation treatment system is within the treatment region, and
    the method includes:
      determining whether a first region exists, wherein the first region forms when one or more leaves of the first group of the first layer of leaves pass across a first line such that the first region is exposed to allow at least a portion of the first portion of the radiation beams to leak through; and
      causing, based on a determination result, at least one of the at least one block or the second layer of leaves of the MLC to operate.

We claim:

1. A radiation treatment system, comprising:
  a radiation source configured to emit radiation beams;
  a multi-leaf collimator (MLC) situated in a first plane, wherein the MLC includes at least one layer of leaves, at least a portion of the leaves of the MLC being movable to block a first portion of the radiation beams within a radiation area, wherein a second portion of the radiation beams is incident at a treatment region of the radiation treatment system; and
  at least one block situated in a second plane different from the first plane, wherein the at least one block is configured to shield leaking radiation beams of the radiation beams leaking through an end area outside the treatment region, wherein
  the treatment region is formed by a front end of the at least a portion of the leaves; and
  the end area is formed by an edge of the radiation area and a rear end of one or more leaves of the at least a portion of the leaves, the rear end of the one or more leaves of the at least a portion of the leaves being within the radiation area.

2. The radiation treatment system of claim 1, wherein the MLC and the at least one block are arranged along a direction of the radiation beams towards an object.

3. The radiation treatment system of claim 1, wherein:
  each of the at least one layer of leaves includes a first group of leaves and a second group of leaves opposing each other, and
  the end area includes a first section that forms when one or more leaves of the first group of at least one of the at least one layer of leaves pass across a first line such that the first section is exposed to allow at least a portion of the leaking radiation beams to leak through.

4. The radiation treatment system of claim 3, wherein:
  the first line is a centerline of the radiation area, and
  a length of at least one of the first group of leaves is equal to a half of a length of the radiation area.

5. The radiation treatment system of claim 3, wherein a size of each of the at least one block relates to at least one of: a first reference distance that at least one leaf of the first group of leaves is allowed to move, a second reference distance that at least one leaf of the second group of leaves is allowed to move, a size of each of the at least one layer of leaves, a length of at least one leaf of the first group of leaves, or a length of at least one leaf of the second group of leaves.

6. The radiation treatment system of claim 1, wherein the at least one block includes a first block and a second block situated in the second plane.

7. The radiation treatment system of claim 1, wherein at least one of the at least one block, or a portion thereof, is movable.

8. The radiation treatment system of claim 1, wherein at least one of the at least one block is fixed, and projection of the at least one of the at least one block on the first plane at least partially overlaps the MLC.

9. The radiation treatment system of claim 1, wherein
  the end area includes a first section that forms when one or more ends of one or more leaves of a group of at least one of the at least one layer of leaves are within a boundary of the radiation area such that the first section is exposed to allow at least a portion of the first portion of the radiation beams to leak through.

10. A method for operating a multi-leaf collimator (MLC), the method being implemented on a computing device having at least one processor, and at least one computer-readable storage medium, wherein:
  the MLC includes a first layer of leaves and a second layer of leaves, each of the first layer of leaves and the second layer of leaves includes a first group of leaves and a second group of leaves, at least a portion of the leaves of the MLC is movable to block a first portion of radiation beams within a radiation area, and a second portion of the radiation beams is incident at a treatment region of the radiation treatment system, and
  the method includes:
    determining whether a first region outside the treatment region exists, wherein
      the treatment region is formed by a front end of one or more leaves of the first layer of leaves; and
      the first region is formed by an edge of the radiation area and a rear end of at least one of the one or more leaves of the first layer of leaves, the rear end of the at least one of the one or more leaves of the first layer of leaves being within the radiation area such that at least a portion of the radiation beams leaks through the first region; and causing, based on a determination result, the second layer of leaves of the MLC to operate.

11. The method of claim 10, wherein:
the first region forms when the at least one of the one or more leaves of the first layer of leaves passes across a first line;
the first line is a centerline of the radiation area, and
a length of at least one of the first group of leaves is equal to a half of a length of the radiation area.

12. The method of claim 10, wherein the determination result includes that the first region exists, and the causing the second layer of leaves of the MLC to operate includes:
causing one or more leaves of the second layer of leaves to move to shield the at least a portion of the radiation beams leaking through the first region.

13. The method of claim 10, wherein the determination result includes that the first region does not exist, and the causing the second layer of leaves of the MLC to operate includes:
causing one or more leaves of the second layer of leaves to move to block a part of the second portion of the radiation beams.

14. A method for operating a radiation treatment system, the method being implemented on a computing device having at least one processor, and at least one computer-readable storage medium, wherein:
the radiation treatment system includes a multi-leaf collimator (MLC) and at least one block, the MLC includes at least one layer of leaves, each of the at least one layer of leaves includes a first group of leaves and a second group of leaves, at least a portion of the leaves of the MLC is movable to block a first portion of radiation beams within a radiation area, and a second portion of the radiation beams is incident at a treatment region of the radiation treatment system, and
the method includes:
determining whether a first region outside the treatment region exists, wherein
the treatment region is formed by a front end of the at least a portion of the leaves; and
the first region is formed by an edge of the radiation area and a rear end of one or more leaves of the at least a portion of the leaves, the rear end of the one or more leaves of the at least a portion of the leaves being within the radiation area such that at least a portion of the radiation beams leaks through the first region; and causing, based on a determination result, at least one of the at least one block or a second layer of leaves of the MLC to operate.

15. The method of claim 14, wherein the at least one block is fixed, and projection of the at least one of the at least one block at least partially overlaps the MLC.

16. The method of claim 15, wherein the determination result includes that the first region exists, and the causing at least one of the at least one block or the second layer of leaves of the MLC to operate includes:
causing one or more leaves of the second layer of leaves to move to block a part of the second portion of the radiation beams.

17. The method of claim 14, wherein the at least one block is moveable, the determination result includes that the first region exists, and the causing at least one of the at least one block or the second layer of leaves of the MLC to operate includes:
determining whether the at least one block is able to move; and
causing, based on a second determination result, the second layer of leaves to operate.

18. The method of claim 17, wherein the causing, based on a second determination result, the second layer of leaves to operate includes:
in response to the second determination that the at least one block is able to move, causing the at least one block to shield the at least a portion of the radiation beams that leak through the first region, and causing one or more leaves of the second layer of leaves to move to block a part of the second portion of the radiation beams; or
in response to the second determination that the at least one block is unable to move, causing one or more leaves of the second layer of leaves to shield the at least a portion of the radiation beams that leak through the first region.

19. The method of claim 14, wherein the determination result includes that the first region does not exist, and the causing at least one of the at least one block or the second layer of leaves of the MLC to operate includes:
causing one or more leaves of the second layer of leaves to move to block a part of the second portion of the radiation beams.

20. The method of claim 14, wherein the MLC and the at least one block are arranged along a direction of the radiation beams towards an object.

* * * * *